United States Patent [19]

Lee et al.

[11] Patent Number: 5,776,457
[45] Date of Patent: Jul. 7, 1998

[54] ANTIBODIES TO HUMAN PF4A RECEPTOR AND COMPOSITIONS THEREOF

[75] Inventors: James Lee, San Bruno; William I. Wood, San Mateo, both of Calif.

[73] Assignee: Genentech, Inc., South San Francisco, Calif.

[21] Appl. No.: 701,265

[22] Filed: Aug. 22, 1996

Related U.S. Application Data

[63] Continuation of Ser. No. 664,228, Jun. 7, 1996, abandoned, which is a continuation of Ser. No. 76,093, Jun. 11, 1993, Pat. No. 5,543,503, which is a continuation-in-part of Ser. No. 810,782, Dec. 19, 1991, abandoned, which is a continuation-in-part of Ser. No. 677,211, Mar. 29, 1991, abandoned.

[51] Int. Cl.$^6$ .................. C07K 16/00; C12P 21/08; A61K 39/395
[52] U.S. Cl. .................. 424/139.1; 424/143.1; 530/387.9; 530/387.6; 530/388.22; 435/7.24
[58] Field of Search .................. 530/387.1, 387.9, 530/388.1, 388.22, 389.6; 435/7.24; 424/143.1, 152.1, 139.1

[56] References Cited

PUBLICATIONS

Kahan et al., Current Opinion in Immunology, 4: 553–560, Jul. 1992.
Thomas et al., J. of Biol. Chem., 265:20061–20064, Nov. 1990.
Beckmann et al., Biochem. and Biophys. Res. Commun., 179:784–789, Jul. 1991.
Lerner, Nature, 299:592–596, Oct. 1982.
Antibodies A Laboratory Manual, Harlow and Lane, Cold Spring Harbor Press, Jan. 1988.
Sevier et al., Clin Chem. 27:1797–1806, Nov. 1981.
Federsppiel et al., "Molecular cloning of the cDNA and chromosomal localization of the gene for a putative seven–transmembrane segment (7–TMS) receptor isolated from human spleen" *Genomics* 16:707–712 (1993).
Feng, Yu et al., "HIV–1 entry cofactor: functional cDNA cloning of a seven–transmembrane, G protein–coupled receptor" *Science* 272:872–877 (1996).
Jazin et al., "A proposed bovine neuropeptide Y (NPY) receptor cDNA clone, or its human homologue, confers neither NPY binding sites nor NPY responsiveness on transfected cells" *Regulatory Peptides* 47:247–258 (1993).
Loetscher et al., "Cloning of a human seven–transmembrane domain receptor, LESTR, that is highly expressed in leukocytes" *Journal of Biological Chemistry* 269(1):232–237 (1994).
Nomura, H. et al., "Molecular cloning of cDNAs encoding a LD78 receptor and putative leukocyte chemotactic peptide receptors" *International Immunology* 5(10):1239–1249 (1993).
Herzog et al., "Molecular cloning, characterization, and localization of the human homolog to the reported bovine NPY Y3 receptor: lack of NPY binding and activation" *DNA and Cell Biology* 12(6): 465–471 (1993).

*Primary Examiner*—Frank C. Eisenschenk
*Assistant Examiner*—Patrick Nolan
*Attorney, Agent, or Firm*—Richard B. Love

[57] ABSTRACT cDNAs encoding a class of receptors, including the IL-8 receptors, have been identified in human tissue. Recombinantly produced PF4ARs are used in the preparation and purification of antibodies capable of binding to the receptors, and in diagnostic assays. The antibodies are advantageously used in the prevention and treatment of inflammatory conditions.

5 Claims, 17 Drawing Sheets

```
    ATG TCA AAT ATT ACA GAT CCA CAG ATG TGG GAT TTT  86
    Met Ser Asn Ile Thr Asp Pro Gln Met Trp Asp Phe
    1               5                   10

GAT GAT CTA AAT TTC ACT GGC ATG CCA CCT GCA GAT GAA 125
Asp Asp Leu Asn Phe Thr Gly Met Pro Pro Ala Asp Glu
        15                  20                  25

GAT TAC AGC CCC TGT ATG CTA GAA ACT GAG ACA CTC AAC 164
Asp Tyr Ser Pro Cys Met Leu Glu Thr Glu Thr Leu Asn
                30                  35

AAG TAT GTT GTG ATC ATC GCC TAT GCC CTA GTG TTC CTG 203
Lys Tyr Val Val Ile Ile Ala Tyr Ala Leu Val Phe Leu
    40                  45                  50

CTG AGC CTG CTG GGA AAC TCC CTG GTG ATG CTG GTC ATC 242
Leu Ser Leu Leu Gly Asn Ser Leu Val Met Leu Val Ile
            55                  60

TTA TAC AGC AGG GTC GGC CGC TCC GTC ACT GAT GTC TAC 281
Leu Tyr Ser Arg Val Gly Arg Ser Val Thr Asp Val Tyr
65                  70                  75

CTG CTG AAC CTG GCC TTG GCC GAC CTA CTC TTT GCC CTG 320
Leu Leu Asn Leu Ala Leu Ala Asp Leu Leu Phe Ala Leu
        80                  85                  90

ACC TTG CCC ATC TGG GCC GCC TCC AAG GTG AAT GGC TGG 359
Thr Leu Pro Ile Trp Ala Ala Ser Lys Val Asn Gly Trp
                95                  100

ATT TTT GGC ACA TTC CTG TGC AAG GTG GTC TCA CTC CTG 398
Ile Phe Gly Thr Phe Leu Cys Lys Val Val Ser Leu Leu
    105                 110                 115

AAG GAA GTC AAC TTC TAC AGT GGC ATC CTG CTG TTG GCC 437
Lys Glu Val Asn Phe Tyr Ser Gly Ile Leu Leu Leu Ala
            120                 125

TGC ATC AGT GTG GAC CGT TAC CTG GCC ATT GTC CAT GCC 476
Cys Ile Ser Val Asp Arg Tyr Leu Ala Ile Val His Ala
130                 135                 140

ACA CGC ACA CTG ACC CAG AAG CGT CAC TTG GTC AAG TTT 515
Thr Arg Thr Leu Thr Gln Lys Arg His Leu Val Lys Phe
        145                 150                 155

GTT TGT CTT GGC TGC TGG GGA CTG TCT ATG AAT CTG TCC 554
Val Cys Leu Gly Cys Trp Gly Leu Ser Met Asn Leu Ser
                160                 165

CTG CCC TTC TTC CTT TTC CGC CAG GCT TAC CAT CCA AAC 593
Leu Pro Phe Phe Leu Phe Arg Gln Ala Tyr His Pro Asn
    170                 175                 180

AAT TCC AGT CCA GTT TGC TAT GAG GTC CTG GGA AAT GAC 632
Asn Ser Ser Pro Val Cys Tyr Glu Val Leu Gly Asn Asp
            185                 190

ACA GCA AAA TGG CGG ATG GTG TTG CGG ATC CTG CCT CAC 671
Thr Ala Lys Trp Arg Met Val Leu Arg Ile Leu Pro His
195                 200                 205
```

FIG. 2A

```
ACC TTT GGC TTC ATC GTG CCG CTG TTT GTC ATG CTG TTC  710
Thr Phe Gly Phe Ile Val Pro Leu Phe Val Met Leu Phe
        210             215             220

TGC TAT GGA TTC ACC CTG CGT ACA CTG TTT AAG GCC CAC  749
Cys Tyr Gly Phe Thr Leu Arg Thr Leu Phe Lys Ala His
                225             230

ATG GGG CAG AAG CAC CGA GCC ATG AGG GTC ATC TTT GCT  788
Met Gly Gln Lys His Arg Ala Met Arg Val Ile Phe Ala
        235             240             245

GTC GTC CTC ATC TTC CTG CTT TGC TGG CTG CCC TAC AAC  827
Val Val Leu Ile Phe Leu Leu Cys Trp Leu Pro Tyr Asn
            250             255

CTG GTC CTG CTG GCA GAC ACC CTC ATG AGG ACC CAG GTG  866
Leu Val Leu Leu Ala Asp Thr Leu Met Arg Thr Gln Val
260             265             270

ATC CAG GAG ACC TGT GAG CGC CGC AAC AAC ATC GGC CGG  905
Ile Gln Glu Thr Cys Glu Arg Arg Asn Asn Ile Gly Arg
        275             280             285

GCC CTG GAT GCC ACT GAG ATT CTG GGA TTT CTC CAT AGC  944
Ala Leu Asp Ala Thr Glu Ile Leu Gly Phe Leu His Ser
                290             295

TGC CTC AAC CCC ATC ATC TAC GCC TTC ATC GGC CAA AAT  983
Cys Leu Asn Pro Ile Ile Tyr Ala Phe Ile Gly Gln Asn
    300             305             310

TTT CGC CAT GGA TTC CTC AAG ATC CTG GCT ATG CAT GGC  1022
Phe Arg His Gly Phe Leu Lys Ile Leu Ala Met His Gly
            315             320

CTG GTC AGC AAG GAG TTC TTG GCA CGT CAT CGT GTT ACC  1061
Leu Val Ser Lys Glu Phe Leu Ala Arg His Arg Val Thr
325             330             335

TCC TAC ACT TCT TCG TCT GTC AAT GTC TCT TCC AAC CTC  1100
Ser Tyr Thr Ser Ser Ser Val Asn Val Ser Ser Asn Leu
        340             345             350

TGAAAACCAT CGATGAAGGA ATATCTCTTC TCAGAAGGAA AGAATAACCA  1150

ACACCCTGAG GTTGTGTGTG GAAGGTGATC TGGCTCTGGA CAGGCACTAT  1200

CTGGGTTTTG GGGGACGCT ATAGGATGTG GGGAAGTTAG GAACTGGTGT  1250

CTTCAGGGGC CACACCAACC TTCTGAGGAG CTGTTGAGGT ACCTCCAAGG  1300

ACCGGCCTTT GCACCTCCAT GGAAACGAAG CACCATCATT CCCGTTGAAC  1350

GTCACATCTT TAACCCACTA ACTGGCTAAT TAGCATGGCC ACATCTGAGC  1400

CCCGAATCTG ACATTAGATG AGAGAACAGG GCTGAAGCTG TGTCCTCATG  1450
```

FIG. 2B

```
AGGGCTGGAT GCTCTCGTTG ACCCTCACAG GAGCATCTCC TCAACTCTGA 1500

GTGTTAAGCG TTGAGCCACC AAGCTGGTGG CTCTGTGTGC TCTGATCCGA 1550

GCTCAGGGGG GTGGTTTTCC CATCTCAGGT GTGTTGCAGT GTCTGCTGGA 1600

GACATTGAGG CAGGCACTGC CAAAACATCA ACCTGCCAGC TGGCCTTGTG 1650

AGGAGCTGGA AACACATGTT CCCCTTGGGG GTGGTGGATG AACAAAGAGA 1700

AAGAGGGTTT GGAAGCCAGA TCTATGCCAC AAGAACCCCC TTTACCCCCA 1750

TGACCAACAT CGCAGACACA TGTGCTGGCC ACCTGCTGAG CCCCAAGTGG 1800

AACGAGACAA GCAGCCCTTA GCCCTTCCCC TCTGCAGCTT CCAGGCTGGC 1850

GTGCAGCATC AGCATCCCTA GAAAGCCATG TGCAGCCACC AGTCCATTGG 1900

GCAGGCAGAT GTTCCTAATA AAGCTTCTGT TCC 1933
```

FIG. 2C

```
                                                                    GAATTCCAGT GTGCTGGCGG CGCGGCGCAA AGTGACGCCG AGGGCCTGAG  50

TGCTCCAGTA GCCACCGCAT CTGGAGAACC AGCGGTTACC ATG GAG  96
                                              Met Glu
                                              1

GGG ATC AGT ATA TAC ACT TCA GAT AAC TAC ACC GAG GAA  135
Gly Ile Ser Ile Tyr Thr Ser Asp Asn Tyr Thr Glu Glu
            5               10                  15

ATG GGC TCA GGG GAC TAT GAC TCC ATG AAG GAA CCC TGT  174
Met Gly Ser Gly Asp Tyr Asp Ser Met Lys Glu Pro Cys
                20              25

TTC CGT GAA GAA AAT GCT AAT TTC AAT AAA ATC TTC CTG  213
Phe Arg Glu Glu Asn Ala Asn Phe Asn Lys Ile Phe Leu
    30              35                  40

CCC ACC ATC TAC TCC ATC ATC TTC TTA ACT GGC ATT GTG  252
Pro Thr Ile Tyr Ser Ile Ile Phe Leu Thr Gly Ile Val
            45                  50

GGC AAT GGA TTG GTC ATC CTG GTC ATG GGT TAC CAG AAG  291
Gly Asn Gly Leu Val Ile Leu Val Met Gly Tyr Gln Lys
55              60                  65

AAA CTG AGA AGC ATG ACG GAC AAG TAC AGG CTG CAC CTG  330
Lys Leu Arg Ser Met Thr Asp Lys Tyr Arg Leu His Leu
        70              75                      80

TCA GTG GCC GAC CTC CTC TTT GTC ATC ACG CTT CCC TTC  369
Ser Val Ala Asp Leu Leu Phe Val Ile Thr Leu Pro Phe
                85                  90

TGG GCA GTT GAT GCC GTG GCA AAC TGG TAC TTT GGG AAC  408
Trp Ala Val Asp Ala Val Ala Asn Trp Tyr Phe Gly Asn
        95              100                 105

TTC CTA TGC AAG GCA GTC CAT GTC ATC TAC ACA GTC AAC  447
Phe Leu Cys Lys Ala Val His Val Ile Tyr Thr Val Asn
            110                 115

CTC TAC AGC AGT GTC CTC ATC CTG GCC TTC ATC AGT CTG  486
Leu Tyr Ser Ser Val Leu Ile Leu Ala Phe Ile Ser Leu
120                 125                 130

GAC CGC TAC CTG GCC ATC GTC CAC GCC ACC AAC AGT CAG  525
Asp Arg Tyr Leu Ala Ile Val His Ala Thr Asn Ser Gln
        135                 140                 145

AGG CCA AGG AAG CTG TTG GCT GAA AAG GTG GTC TAT GTT  564
Arg Pro Arg Lys Leu Leu Ala Glu Lys Val Val Tyr Val
                150                 155

GGC GTC TGG ATC CCT GCC CTC CTG CTG ACT ATT CCC GAC  603
Gly Val Trp Ile Pro Ala Leu Leu Leu Thr Ile Pro Asp
160                 165                 170

TTC ATC TTT GCC AAC GTC AGT GAG GCA GAT GAC AGA TAT  642
Phe Ile Phe Ala Asn Val Ser Glu Ala Asp Asp Arg Tyr
            175                 180
```

FIG. 4A

```
ATC TGT GAC CGC TTC TAC CCC AAT GAC TTG TGG GTG GTT 681
Ile Cys Asp Arg Phe Tyr Pro Asn Asp Leu Trp Val Val
185             190             195

GTG TTC CAG TTT CAG CAC ATC ATG GTT GGC CTT ATC CTG 720
Val Phe Gln Phe Gln His Ile Met Val Gly Leu Ile Leu
    200             205             210

CCT GGT ATT GTC ATC CTG TCC TGC TAT TGC ATT ATC ATC 759
Pro Gly Ile Val Ile Leu Ser Cys Tyr Cys Ile Ile Ile
            215             220

TCC AAG CTG TCA CAC TCC AAG GGC CAC CAG AAG CGC AAG 798
Ser Lys Leu Ser His Ser Lys Gly His Gln Lys Arg Lys
    225             230             235

GCC CTC AAG ACC ACA GTC ATC CTC ATC CTG GCT TTC TTC 837
Ala Leu Lys Thr Thr Val Ile Leu Ile Leu Ala Phe Phe
            240             245

GCC TGT TGG CTG CCT TAC TAC ATT GGG ATC AGC ATC GAC 876
Ala Cys Trp Leu Pro Tyr Tyr Ile Gly Ile Ser Ile Asp
250             255             260

TCC TTC ATC CTC CTG GAA ATC ATC AAG CAA GGG TGT GAG 915
Ser Phe Ile Leu Leu Glu Ile Ile Lys Gln Gly Cys Glu
        265             270             275

TTT GAG AAC ACT GTG CAC AAG TGG ATT TCC ATC ACC GAG 954
Phe Glu Asn Thr Val His Lys Trp Ile Ser Ile Thr Glu
                280             285

GCC CTA GCT TTC TTC CAC TGT TGT CTG AAC CCC ATC CTC 993
Ala Leu Ala Phe Phe His Cys Cys Leu Asn Pro Ile Leu
290             295             300

TAT GCT TTC CTT GGA GCC AAA TTT AAA ACC TCT GCC CAG 1032
Tyr Ala Phe Leu Gly Ala Lys Phe Lys Thr Ser Ala Gln
        305             310

CAC GCA CTC ACC TCT GTG AGC AGA GGG TCC AGC CTC AAG 1071
His Ala Leu Thr Ser Val Ser Arg Gly Ser Ser Leu Lys
315             320             325

ATC CTC TCC AAA GGA AAG CGA GGT GGA CAT TCA TCT GTT 1110
Ile Leu Ser Lys Gly Lys Arg Gly Gly His Ser Ser Val
        330             335             340

TCC ACT GAG TCT GAG TCT TCA AGT TTT CAC TCC AGC TAAC 1150
Ser Thr Glu Ser Glu Ser Ser Ser Phe His Ser Ser
            345             350         352

ACAGATGTAA AAGACTTTTT TTTATACGAT AAATAACTTT TTTTTAAGTT 1200

ACACATTTTT CAGATATAAA AGACTGACCA ATATTGTACA GTTTTTATTG 1250

CTTGTTGGAT TTTTGTCTTG TGTTTCTTTA GTTTTTGTGA AGTTTAATTG 1300

ACTTATTTAT ATAAATTTTT TTTGTTTCAT ATTGATGTGT GTCTAGGCAG 1350
```

FIG. 4B

| | | | | |
|---|---|---|---|---|
| GACCTGTGGC | CAAGTTCTTA | GTTGCTGTAT | GTCTCGTGGT | AGGACTGTAG 1400 |
| AAAAGGGAAC | TGAACATTCC | AGAGCGTGTA | GTGAATCACG | TAAAGCTAGA 1450 |
| AATGATCCCC | AGCTGTTTAT | GCATAGATAA | TCTCTCCATT | CCCGTGGAAC 1500 |
| GTTTTTCCTG | TTCTTAAGAC | GTGATTTTGC | TGTAGAAGAT | GGCACTTATA 1550 |
| ACCAAAGCCC | AAAGTGGTAT | AGAAATGCTG | GTTTTTCAGT | TTTCAGGAGT 1600 |
| GGGTTGATTT | CAGCACCTAC | AGTGTACAGT | CTTGTATTAA | GTTGTTAATA 1650 |
| AAAGTACATG | TTAAACTTAA | AAAAAAAAAA | AAAAAAAAAA | AAAAAAAAAA 1700 |
| AAAAAAAAAA | AAAGCGGCCG | CCAGCACACT | GGAATTC 1737 | |

FIG. 4C

```
GAATTCCAGT GTGCTGGCGG CCGCCCAGTG TGCTGGCGGC GGCAGTTGAG  50

GGAAAGGACA GAGGTTATGA GTGCCTGCAA GAGTGGCAGC CTGGAGTAGA 100

GAAAACACTA AAGGTGGAGT CAAAAGACCT GAGTTCAAGT CCCAGCTCTG 150

CCACTGGTTA GCTGTGGGAT CTCGGAAAAG ACCCAGTGAA AAAAAAAAAA 200

AAAGTGATGA GTTGTGAGGC AGGTCGCGGC CCTACTGCCT CAGGAGACGA 250

TGCGCAGCTC ATTTGCTTAA ATTTGCAGCT GACGGCTGCC ACCTCTCTAG 300

AGGCACCTGG CGGGGAGCCT CTCAACATAA GACAGTGACC AGTCTGGTGA 350
```

```
CTCACAGCCG GCACAGCC ATG AAC TAC CCG CTA ACG CTG GAA 392
                    Met Asn Tyr Pro Leu Thr Leu Glu
                     1               5
```

```
ATG GAC CTC GAG AAC CTG GAG GAC CTG TTC TGG GAA CTG 431
Met Asp Leu Glu Asn Leu Glu Asp Leu Phe Trp Glu Leu
     10              15                  20
```

```
GAC AGA TTG GAC AAC TAT AAC GAC ACC TCC CTG GTG GAA 470
Asp Arg Leu Asp Asn Tyr Asn Asp Thr Ser Leu Val Glu
             25                  30
```

```
AAT CAT CTC TGC CCT GCC ACA GAG GGG CCC CTC ATG GCC 509
Asn His Leu Cys Pro Ala Thr Glu Gly Pro Leu Met Ala
 35                  40                  45
```

```
TCC TTC AAG GCC GTG TTC GTG CCC GTG GCC TAC AGC CTC 548
Ser Phe Lys Ala Val Phe Val Pro Val Ala Tyr Ser Leu
         50                  55                  60
```

```
ATC TTC CTC CTG GGC GTG ATC GGC AAC GTC CTG GTG CTG 587
Ile Phe Leu Leu Gly Val Ile Gly Asn Val Leu Val Leu
                 65                  70
```

```
GTG ATC CTG GAG CGG CAC CGG CAG ACA CGC AGT TCC ACG 626
Val Ile Leu Glu Arg His Arg Gln Thr Arg Ser Ser Thr
     75                  80                  85
```

```
GAG ACC TTC CTG TTC CAC CTG GCC GTG GCC GAC CTC CTG 665
Glu Thr Phe Leu Phe His Leu Ala Val Ala Asp Leu Leu
             90                  95
```

```
CTG GTC TTC ATC TTG CCC TTT GCC GTG GCC GAG GGC TCT 704
Leu Val Phe Ile Leu Pro Phe Ala Val Ala Glu Gly Ser
100             105                 110
```

```
GTG GGC TGG GTC CTG GGG ACC TTC CTC TGC AAA ACT GTG 743
Val Gly Trp Val Leu Gly Thr Phe Leu Cys Lys Thr Val
        115                 120                 125
```

```
ATT GCC CTG CAC AAA GTC AAC TTC TAC TGC AGC AGC CTG 782
Ile Ala Leu His Lys Val Asn Phe Tyr Cys Ser Ser Leu
                130                 135
```

FIG. 5A

```
CTC CTG GCC TGC ATC GCC GTG GAC CGC TAC CTG GCC ATT   821
Leu Leu Ala Cys Ile Ala Val Asp Arg Tyr Leu Ala Ile
        140             145                 150

GTC CAC GCC GTC CAT GCC TAC CGC CAC CGC CGC CTC CTC   860
Val His Ala Val His Ala Tyr Arg His Arg Arg Leu Leu
            155                 160

TCC ATC CAC ATC ACC TGT GGG ACC ATC TGG CTG GTG GGC   899
Ser Ile His Ile Thr Cys Gly Thr Ile Trp Leu Val Gly
165                 170                 175

TTC CTC CTT GCC TTG CCA GAG ATT CTC TTC GCC AAA GTC   938
Phe Leu Leu Ala Leu Pro Glu Ile Leu Phe Ala Lys Val
        180             185                 190

AGC CAA GGC CAT CAC AAC AAC TCC CTG CCA CGT TGC ACC   977
Ser Gln Gly His His Asn Asn Ser Leu Pro Arg Cys Thr
                195                 200

TTC TCC CAA GAG AAC CAA GCA GAA ACG CAT GCC TGG TTC  1016
Phe Ser Gln Glu Asn Gln Ala Glu Thr His Ala Trp Phe
205                 210                 215

ACC TCC CGA TTC CTC TAC CAT GTG GCG GGA TTC CTG CTG  1055
Thr Ser Arg Phe Leu Tyr His Val Ala Gly Phe Leu Leu
            220                 225

CCC ATG CTG GTG ATG GGC TGG TGC TAC GTG GGG GTA GTG  1094
Pro Met Leu Val Met Gly Trp Cys Tyr Val Gly Val Val
230                 235                 240

CAC AGG TTG CGC CAG GCC CAG CGG CGC CCT CAG CGG CAG  1133
His Arg Leu Arg Gln Ala Gln Arg Arg Pro Gln Arg Gln
            245                 250                 255

AAG GCA GTC AGG GTG GCC ATC CTG GTG ACA AGC ATC TTC  1172
Lys Ala Val Arg Val Ala Ile Leu Val Thr Ser Ile Phe
                260                 265

TTC CTC TGC TGG TCA CCC TAC CAC ATC GTC ATC TTC CTG  1211
Phe Leu Cys Trp Ser Pro Tyr His Ile Val Ile Phe Leu
270                 275                 280

GAC ACC CTG GCG AGG CTG AAG GCC GTG GAC AAT ACC TGC  1250
Asp Thr Leu Ala Arg Leu Lys Ala Val Asp Asn Thr Cys
            285                 290

AAG CTG AAT GGC TCT CTC CCC GTG GCC ATC ACC ATG TGT  1289
Lys Leu Asn Gly Ser Leu Pro Val Ala Ile Thr Met Cys
295                 300                 305

GAG TTC CTG GGC CTG GCC CAC TGC TGC CTC AAC CCC ATG  1328
Glu Phe Leu Gly Leu Ala His Cys Cys Leu Asn Pro Met
        310                 315                 320

CTC TAC ACT TTC GCC GGC GTG AAG TTC CGC AGT GAC CTG  1367
Leu Tyr Thr Phe Ala Gly Val Lys Phe Arg Ser Asp Leu
                325                 330

TCG CGG CTC CTG ACG AAG CTG GGC TGT ACC GGC CCT GCC  1406
Ser Arg Leu Leu Thr Lys Leu Gly Cys Thr Gly Pro Ala
335                 340                 345
```

FIG. 5B

```
TCC CTG TGC CAG CTC TTC CCT AGC TGG CGC AGG AGC AGT  1445
Ser Leu Cys Gln Leu Phe Pro Ser Trp Arg Arg Ser Ser
        350                 355

CTC TCT GAG TCA GAG AAT GCC ACC TCT CTC ACC ACG TTC TA  1486
Leu Ser Glu Ser Glu Asn Ala Thr Ser Leu Thr Thr Phe
360             365                 370     372

GGTC CCAGTGTCCC CTTTTATTGC TGCTTTTCCT TGGGGCAGGC  1530

AGTGATGCTG GATGCTCCTT CCAACAGGAG CTGGGATCCT AAGGGCTCAC  1580

CGTGGCTAAG AGTGTCCTAG GAGTATCCTC ATTTGGGGTA GCTAGAGGAA  1630

CCAACCCCCA TTTCTAGAAC ATCCCGCGGC CGCCAGCACA CTGGAATTC  1679
```

FIG. 5C

ANTIBODIES TO HUMAN PF4A RECEPTOR AND COMPOSITIONS THEREOF

This application is a continuation application of U.S. Ser. No. 08/664,228, filed Jun. 7, 1996, now abandoned, which is a continuation application of U.S. Ser. No. 08/076,093 filed Jun. 11, 1993, now U.S. Pat. No. 5,543,503, which is a continuation-in-part application of U.S. Ser. No. 07/810,782 filed Dec. 19, 1991, now abandoned, which is a continuation-in-part application of U.S. Ser. No. 07/677,211 filed Mar. 29, 1991, now abandoned.

BACKGROUND OF THE INVENTION

1. Field of the Invention

This invention relates to the field of assaying platelet factor 4 superfamily members (hereafter "PF4A") and the preparation of agonists and antagonists to the members of this family, in particular, antibodies to these receptors.

2. Description of Background and Related Art

While interleukin-8 was initially identified as a chemoattractant for neutrophils, and was known to bind a receptor on neutrophils (Samanta et al., *J. Exp. Med.*, 169: 1185–1189 [1989]; Besemer et al., *J. Biol. Chem.*, 264: 17409–17415 [1989]; Grob et al. *J. Biol. Chem.*, 265: 8311–8316 [1990]), it has in addition a wide range of pro-inflammatory activities including the stimulation of degranulation and the upregulation of the cell adhesion molecule MAC-1 and of the complement receptor CR1. Oppenheim et al., *Annu. Rev. Immunol.*, 9: 617–648 (1991).

IL-8 is secreted by many cell types in response to pro-inflammatory stimuli such as IL-1β, TNF, and endotoxin and is a member of a family of ten or more pro-inflammatory cytokines with an $M_r \sim 10,000$. Oppenheim et al., supra. This larger family of proteins is called the platelet factor 4 superfamily. Wolpe et al., *FASEB J.*, 3: 2565–73 (1989). Some members of the platelet factor 4 superfamily, in general the subset referred to as C-X-C peptides (including IL-8), possess neutrophil agonist activity, e.g. neutrophil activating protein-2 (NAP-2), platelet factor 4 and NAP-3 (melanoma growth-stimulating activity [MGSA]/gro), all of which are encoded by genes on human chromosome 4. Other members of this family, the C-C peptides, encoded by genes on human chromosome 17, are not neutrophil agonists, and include RANTES, macrophage chemotactic and activating factor (MCAF). Hereafter "PF4A" means the PF4 superfamily. Oppenheim et al., supra.

The IL-8 receptors are members of the superfamily of seven transmembrane, G-protein linked receptors. Taylor, *Biochem. J.*, 272: 1 (1990). This family of receptors includes several hundred different receptors among which the β-adrenergic receptor (Strader et al., *FASEB*, 3: 1825 [1989]; Dixon et al., *EMBO J.*, 6: 3269 [1987]), the muscarinic and cholinergic receptors (Kubo et al., *Nature*, 323: 411 [1986]; Peralta et al., *EMBO J.*, 6: 3923 [1987]), the c5a and fMet-Leu-Phe receptors. Two types of IL-8 receptors have been described: type A (IL8R-A) (Holmes et al., *Science*, 253: 1278 [1991]) and type B (IL8R-B) (Murphy and Tiffany, *Science*, 253: 1280 [1991]) receptors. These two receptors share 77% amino acid identity and have 29–34% sequence homology to C5a and fMet-Leu-Phe. Holmes et al., supra. IL8R-A has a high affinity (2 nM) for IL-8 only, while IL8R-B has a high affinity (2 nM) for both IL-8 and MGSA. The function and expression level of each receptor on these cells have yet to be determined.

It is an object of this invention to identify receptors for the PF4A superfamily (hereinafter "PF4AR").

It is another object of this invention to obtain DNA encoding or hybridizing to these receptors, and to express the receptors in host cells.

It is an additional object of this invention to provide isolates of PF4AR for diagnostic and therapeutic purposes.

A still further object is to obtain DNA encoding variants of such receptors and to prepare such variants in recombinant cell culture.

A yet further object is to identify and prepare antibodies to receptors for the PF4A superfamily (hereinafter "PF4AR").

It is still another object to provide a method for treating or preventing an inflammatory response in a mammal using an antibody to such receptors.

These and other objects of this invention will be apparent from the specification as a whole.

SUMMARY OF THE INVENTION

These objects are accomplished, in one aspect, by providing an isolated novel PF4AR polypeptide, including polypeptides that are related structurally to the PF4AR. Members of this class of polypeptide are hereafter generically termed PF4AR, and include derivatives and variants thereof.

Either the whole PF4AR molecule or fragments thereof (which also may be synthesized by chemical methods) fused (by recombinant expression or in vitro covalent methods) to an immunogenic polypeptide are used to immunize an animal to raise antibodies against a PF4AR epitope. Anti-PF4AR antibodies are recovered from the serum of immunized animals. Alternatively, monoclonal antibodies are prepared from cells of the immunized animal in conventional fashion.

Thus, in a further aspect, the invention provides an antibody that is capable of binding a PF4AR polypeptide, preferably one that does not cross-react with a receptor capable of binding another PF4 superfamily member. More preferably, the antibody is capable of binding an IL-8 receptor, most preferably an IL-8 type A receptor. Also, the preferred antibody has the isotype IgG1 and/or neutralizes the in vitro activity of a PF4AR polypeptide, preferably of an IL-8 type A receptor.

Specific preferred antibodies herein are the monoclonal antibodies designated 2A4, having ATCC Deposit No. HB 11377, and 9H1, having ATCC Deposit No. HB 11376.

Anti-PF4AR antibodies are useful particularly in the diagnosis (in vitro or in vivo) or (when immobilized on an insoluble matrix) the purification of the PF4AR. The antibodies are also useful in treatment of an inflammatory response in patients. Thus, in another aspect, the invention provides a composition comprising the antibody and a pharmaceutically acceptable carrier, as well as a method for treating an inflammatory disorder which method comprises administering to a mammal in need of such treatment an effective amount of this composition.

Substitutional, deletional, or insertional variants of the PF4AR are prepared by in vitro or recombinant methods and screened for immuno-crossreactivity with the PF4AR and for PF4AR antagonist or agonist activity.

The PF4AR also is derivatized in vitro to prepare immobilized PF4AR and labeled PF4AR, particularly for purposes of diagnosis of PF4AR or its antibodies, or for affinity purification of PF4AR antibodies.

The PF4AR, its derivatives, or its antibodies are formulated into physiologically acceptable vehicles, especially for therapeutic use. Such vehicles include sustained-release formulations of the PF4AR.

In still other aspects, the invention provides an isolated nucleic acid molecule encoding the PF4AR, labeled or unlabeled, and a nucleic acid sequence that is complementary to, or hybridizes under suitable conditions to a nucleic acid sequence encoding the PF4AR.

In addition, the invention provides a replicable vector comprising the nucleic acid molecule encoding the PF4AR operably linked to control sequences recognized by a host transformed by the vector; host cells transformed with the vector; and a method of using a nucleic acid molecule encoding the PF4AR to effect the production of PF4AR, comprising expressing the nucleic acid molecule in a culture of the transformed host cells and recovering the PF4AR from the host cell culture. The nucleic acid sequence is also useful in hybridization assays for PF4AR nucleic acid. The recombinant host cells are particularly useful in assaying the appropriate PF4A members.

In further embodiments, the invention provides a method for producing PF4AR comprising inserting into the DNA of a cell containing the nucleic acid encoding the PF4AR a transcription modulatory element in sufficient proximity and orientation to the PF4AR nucleic acid to influence or destroy transcription of DNA encoding a biologically active PF4AR, with an optional further step comprising culturing the cell containing the transcription modulatory element and the PF4AR nucleic acid.

BRIEF DESCRIPTION OF THE DRAWINGS

FIG. 1-a, competition with unlabelled IL-8 or fMLP. FIG. 1b, Scatchard analysis of the IL-8 competition data; apparent Kd=3.6 nM, average of 820,000 binding sites/cell. Similar competitions with human neutrophils gave Kd=1.1 nM, 31000 binding sites/cell.

FIGS. 2a–2c (hereinafter referred to collectively as FIG. 2) depict the amino acid (SEQ ID NO. 2) and nucleotide (SEQ ID NO. 1) sequences of the IL-8 receptor cDNA insert from clone pRK5B.il8r1.1. There are 4 extracellular segments and 4 intracellular segments, each being separated by one of the transmembrane domains. The extracellular segments are approximately delineated by residues 1-39, 99-111, 134-154, 175-203 and 265-290. The IL-8 receptor contains 3 potential N-linked glycosylation sites in the first extracellular region and 3 more in the third extracellular loop.

FIGS. 4a–c (hereinafter collectively referred to as FIG. 4) depict the DNA sequence (SEQ ID NO.3) and an imputed polypeptide sequence (SEQ ID NO.4) for an additional chemokine superfamily receptor identified by probing lambda libraries from a human monocyte-like cell line (HL-60) and human PBLs using a large fragment of the IL-8 receptor DNA.

FIGS. 5a–c (hereinafter collectively referred to as FIG. 5) depict the DNA sequence (SEQ ID NO. 5) and an imputed polypeptide sequence (SEQ ID NO.6) for yet another chemokine superfamily receptor identified by probing lambda libraries from a human monocyte-like cell line (HL-60) and human PBLs using a large fragment of the IL-8 receptor DNA.

In FIG. 9A the solid bars are peptide 2-19, the diagonal hatched bars to the right of the solid bar are peptide 12-31, the dotted bars to the right of peptide 12-31 are peptide 99-100, the diagonal hatching to the right of peptide 99-100 is peptide 176-187, the vertical striped bars are peptide 187-203, the open bars are peptide 264-276, and the horizontal striped bars are peptide 276-290. In FIG. 9B the solid bars are peptide 2-19, the open bars are peptide 1-14, the dotted bars are peptide 1-11, and the diagonal hatching is peptide 1-13 (IL8R-B).

DETAILED DESCRIPTION OF THE INVENTION

By expression cloning was isolated a cDNA encoding the human neutrophil IL-8 receptor together with two other homologous receptors. The amino acid sequence shows that the IL-8 receptor is a member of the G-protein coupled receptor family with clear similarity (29% amino acid identity) to the human neutrophil receptors for the chemoattractants f-Met-Leu-Phe (Boulay et al., supra) and C5a (Gerard and Gerard, *Nature*, 349: 614–617 [1991]). Although the IL-8 receptor sequence may be the human homologue of what has been identified as the isoform of the rabbit f-Met-Leu-Phe receptor (Thomas et al., *J. Biol. Chem.*, 265: 20061–20064 [1990]), this invention shows that when transfected into mammalian cells, this receptor clone confers high affinity binding to IL-8 and produces a transient $Ca^{++}$ mobilization in response to IL-8 with no binding or response to f-Met-Leu-Phe.

Figure 1A:
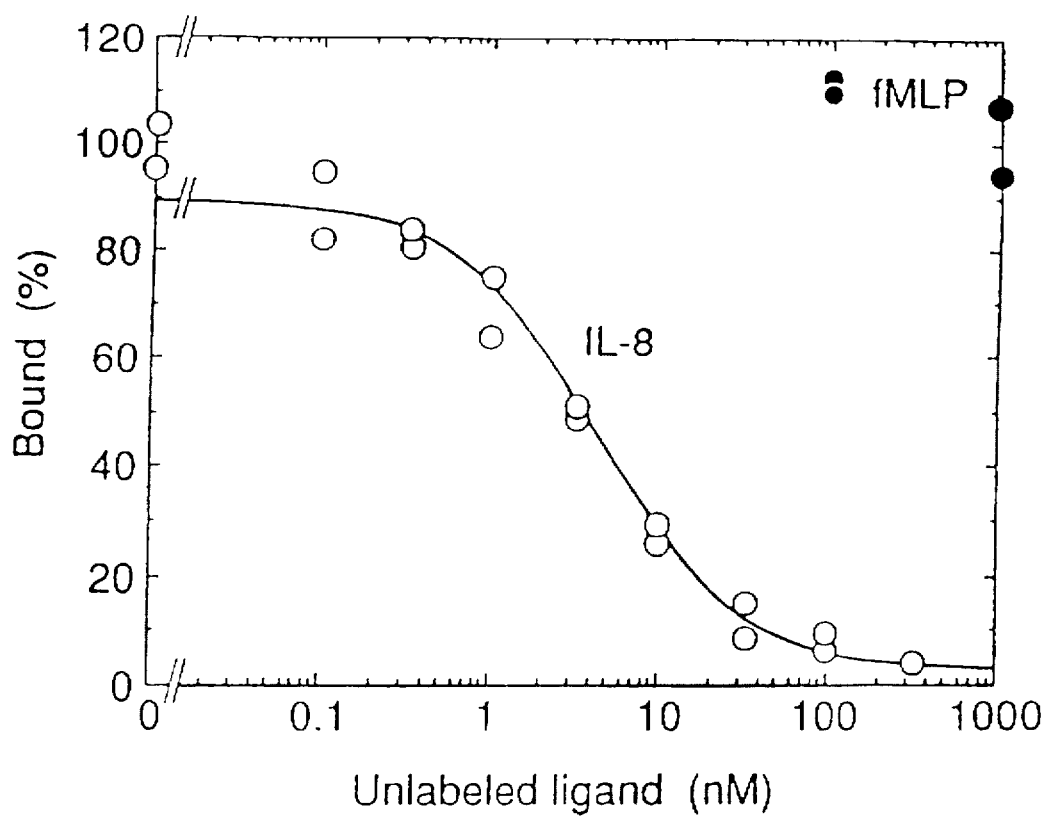
FIGS. 1a–1b depict the high affinity binding of IL-8 to COS cells transfected with clone pRK5B.il8r1.1.
Figure 1B:
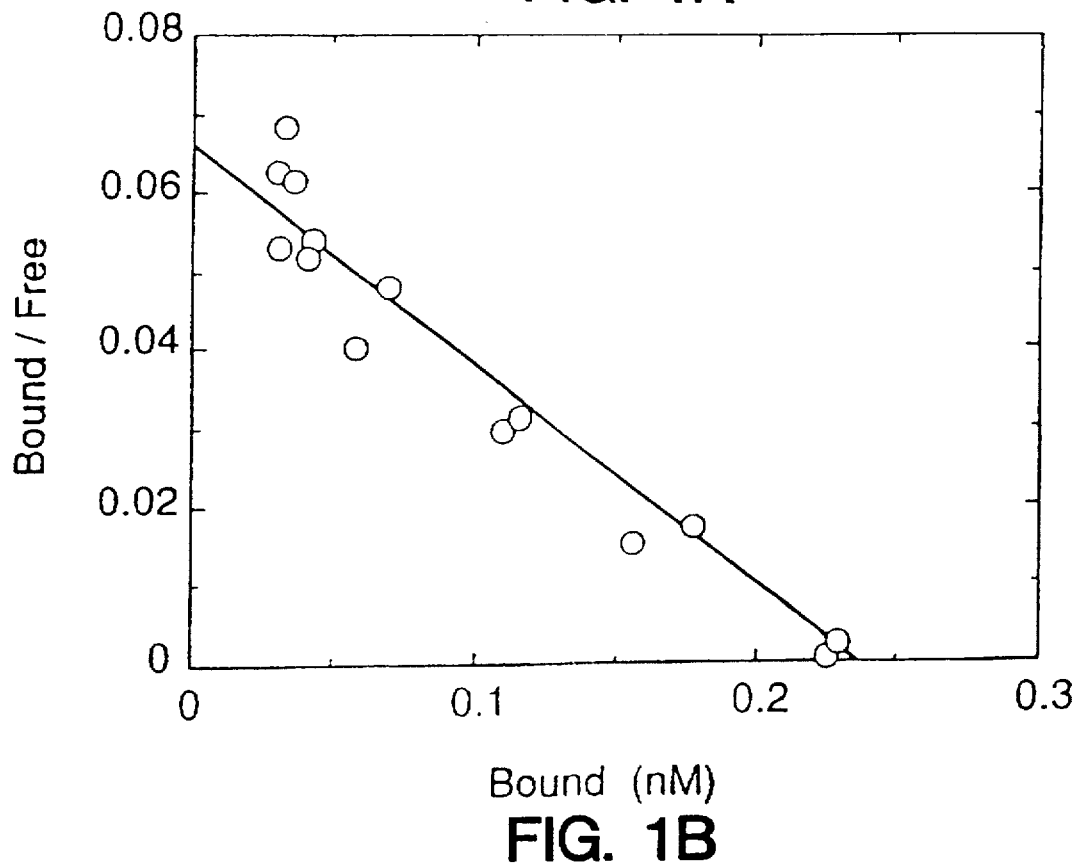
Figure 3A:
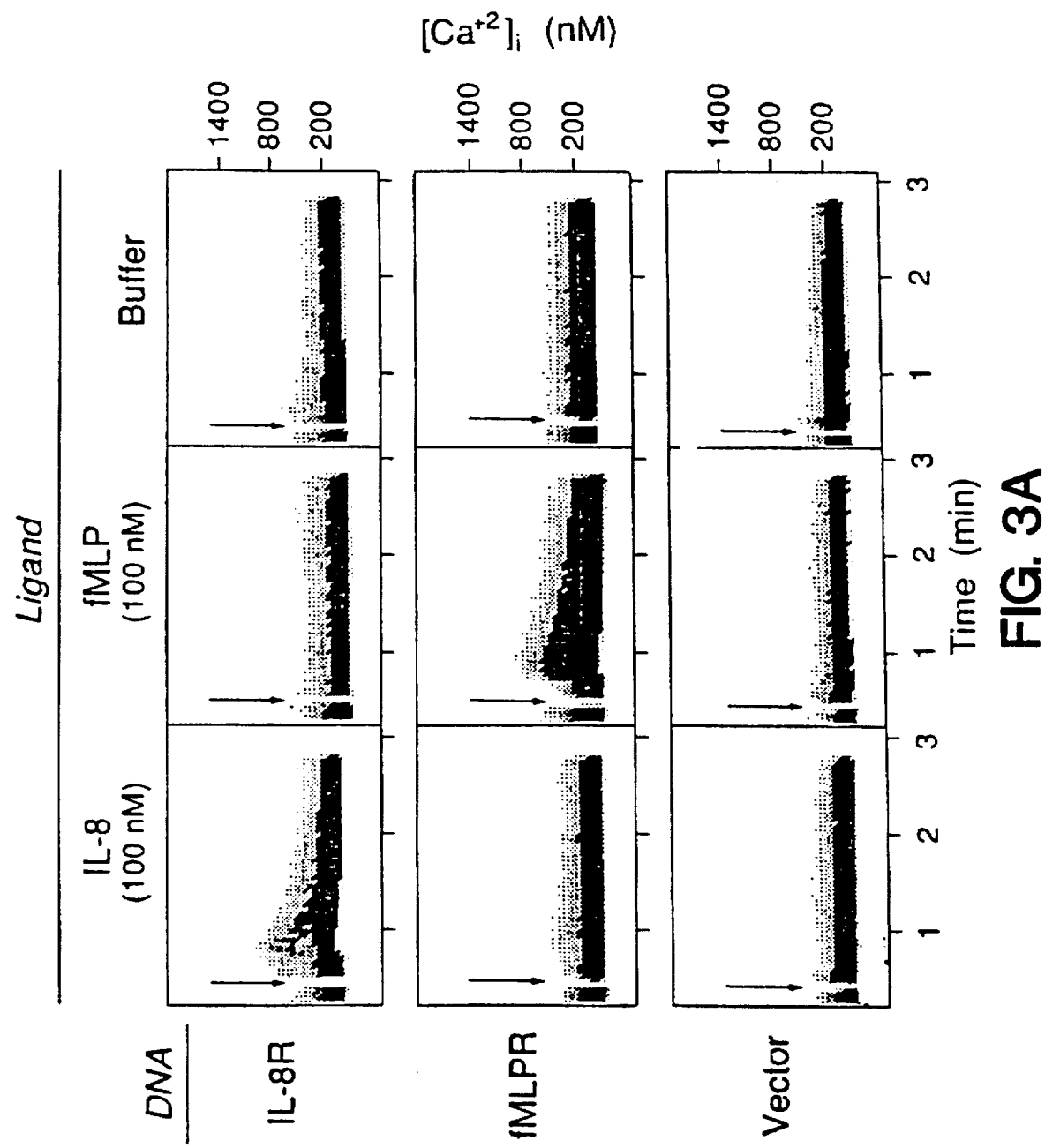
FIG. 3a depicts the flow cytometry determination of the intracellular $Ca^{++}$ response of transfected human IL-8 and fMLP receptors to their ligands. Human embryonic kidney 293 cells were transfected by electroporation (Gearing et al. *EMBO J.*, 8: 3667–3676 [1989]) with IL-8 receptor (clone pRK5B.il8r1.1), fMLP receptor (human fMLP receptor cDNA [Boulay et al., *Biochem. Biophys. Res. Comm.*, 168: 1103–1109 (1990)] in the vector pRK5), or vector (pRK5B; EP 307,247) DNA. After two days, the cells were loaded with 2 µM indo-1 acetoxymethyl ester in RPMI medium (Sigma) for 30 min at 37° C. Intracellular $Ca^{++}$ was measured with a Coulter 753 flow cytometer using the ratio of 405 and 525 nm fluorescence. Grynkiewicz et al., *J. Biol. Chem.*, 260: 3440–3450 (1985).
Figure 3B:
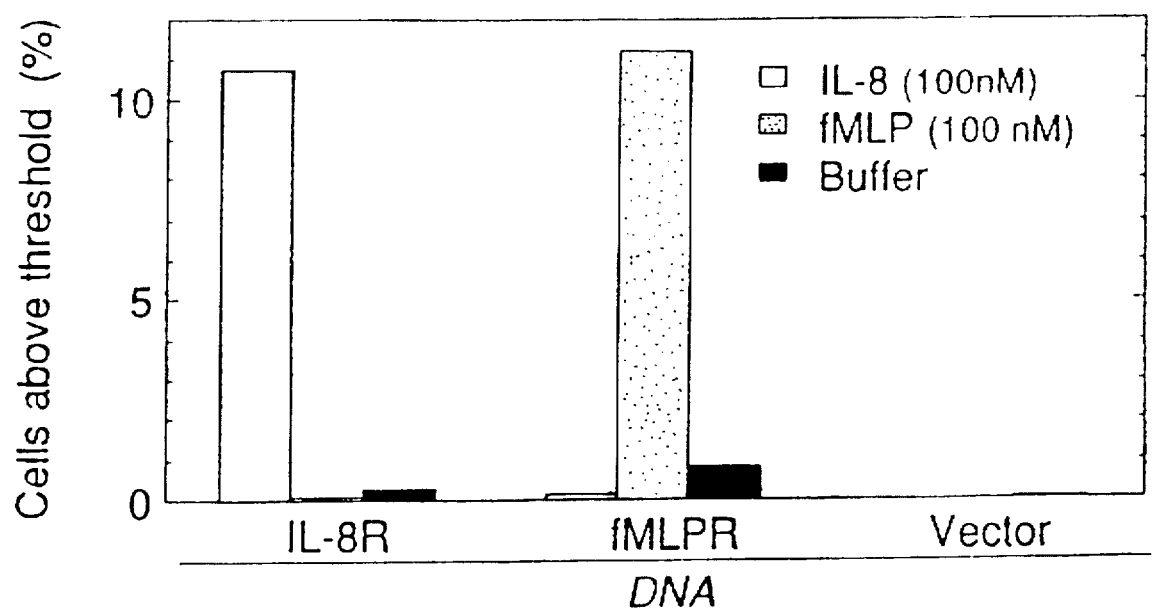
FIG. 3b illustrates the percent of cells above 400M $Ca_i^{++}$ for the time period after addition of IL-8 (about 15 sec. into each run).

A COS cell expression cloning strategy (Sims et al., *Science*, 241: 585–589 [1988]); D'Andrea et al., *Cell*, 57: 277–285 [1989]) was used to isolate clones encoding the IL-8 receptor. A cDNA library constructed from human neutrophil mRNA in the mammalian expression vector pRK5B was transfected into COS-7 cells as pools of 2500 clones, and the cells screened for the binding of $^{125}I$-IL-8. One positive pool from the first 58 transfections was partitioned into smaller pools until a pure clone (pRK5B.il8r1.1) was obtained. FIG. 1 shows the competition of $^{125}I$-IL-8 binding by unlabelled IL-8 to COS cells transfected with the isolated clone. Analysis of this data gives a Kd of 3.6 nM for IL-8 binding which is within the range of 0.8 to 4 nM reported for IL-8 binding to human neutrophils. Samanta et al., supra, Besemer et al., supra, Grob et al., supra. There is no competition of the IL-8 binding by the chemotactic peptide f-Met-Leu-Phe (fMLP).

The DNA sequence of the isolated cDNA clone (FIG. 2) contains a single long open reading frame beginning with a methionine residue that matches the consensus expected for a translation initiation site. Kozak, *Nucleic Acid Res.*, 12: 857–872 (1984). This open reading frame encodes a protein of 350 amino acids (translated M,39.5 kD). The amino acid sequence shares several features with the G-protein coupled receptors of the rhodopsin superfamily including seven hydrophobic domains that are presumed to span the cell membrane and N-linked glycosylation sites near the N-terminus (Dixon et al., *Cold Spring Harb. Sym. Quant. Biol.*, 53: 487–497 [1988]) (see below).

The encoded amino acid sequence is the most similar to a recently cloned sequence for the rabbit fMLP receptor. Thomas et al., supra. The similarity is sufficiently high (79% amino acid identity overall with multiple stretches of more than 20 contiguous amino acid matches) that these two sequences may well be species homologs of the same receptor. The human fMLP receptor has also been cloned (Boulay et al., supra); it has only 26% amino acid identity with the rabbit fMLP receptor (and 29% identity to the human IL-8 receptor presented here). The considerable divergence between the rabbit and human fMLP receptor amino acid sequences has lead to the suggestion in the art (now believed to be possibly erroneous) that these may be two isoforms of the fMLP receptor. Thomas et al., supra.

Neutrophils respond to the chemoattractants IL-8 and fMLP with a rapid, transient increase in the intracellular free $Ca^{++}$ concentration. Oppenheim et al., supra; Korchak et al., *J. Biol Chem.*, 259: 4076–4082 (1984). In order to verify the identification of the clone isolated here as the IL-8 receptor, we have determined the intracellular $Ca^{++}$ response of transfected cells to added IL-8 as well as fMLP. We have used parallel experiments with transfected human fMLP receptor or with the expression vector as controls. Flow cytometer analysis shows a clear transient increase in intracellular $Ca^{++}$ for the transfected IL-8 receptor in response to IL-8. No response is found to fMLP. Conversely, cells transfected with the human fMLP receptor respond to fMLP but not to IL-8. No response to either chemoattractant is found in vector transfected cells. Only a subset of the cells are expected to respond in these experiments as the transfection efficiency is estimated to be 15–25%. Binding experiments (Tennenberg et al., *J. Immunol.*, 141: 3937–3944 [1988]) also failed to detect any binding of $^3H$-fMLP to the expressed IL-8 receptor or $^{125}I$-IL-8 to the expressed human fMLP receptor. These experiments clearly demonstrate the specificity of the two receptors for their respective ligands; a result expected based on the lack of binding competition between IL-8 and fMLP for neutrophils. Oppenheim et al., supra. These results also demonstrate that the cloned receptors function in second message signaling in response to ligand binding.

Blot hybridization of the cloned IL-8 receptor cDNA to human neutrophil mRNA, shows strong bands of 2.4 and 3.0 kb as well as a fainter band at 3.5 kb. While it is clear from the DNA sequence data presented in FIG. 2 that the mRNA for the receptor has a long 3' untranslated region, additional work will be needed to establish whether the multiple RNA bands are due to multiple polyadenylation sites. No hybridization was detected to mRNA from U266 or Jurkat cell lines, which are of the B cell and T cell lineages. No hybridization was found for mRNA from the monocyte cell line U937 as well, in spite of the reports of low levels of IL-8 binding to these cells. Besemer et al., supra; Grob et al., supra.

Alignment of the receptor sequences for the three neutrophil chemoattractants IL-8, fMLP (Boulay et al., supra), and C5a (Gerard and Gerard, supra) shows that they form a subfamily of the G-protein coupled receptors with 29–34% amino acid identity. This subfamily has a short third intracellular loop as compared with other G-protein coupled receptors such as the β-adrenergic (Dixon et al., supra) or muscarinic acetylcholine receptors. Ramachandran, et al., *BioEssays*, 10: 54–57 (1989). This loop contains determinants at least partially responsible for the binding of G-proteins to the receptors. Dixon et al., supra. The intracellular C-terminal region of the IL-8 receptor, while not very similar to that of the fMLP and C5a receptors does preserve a high number of serine and threonine residues that may function as phosphorylation sites. As has been noted for the C5a receptor (Gerard and Gerard, supra), the N-terminal extracellular region for the IL-8 receptor has several acidic residues. These may aid in the binding of IL-8, which is quite basic (pI~9.5).

I. Definitions

In general, the following words or phrases have the indicated definition when used in the description, examples, and claims:

The term "PF4AR" is defined as a polypeptide having a qualitative biological activity in common with the polypeptides of FIGS. 2, 4, or 5. Optionally, PF4AR will have at least 30% and ordinarily 75% amino acid sequence identity with any of the polypeptides of FIGS. 2, 4 or 5. Optionally, PF4AR excludes the rabbit fMLP receptor (Thomas et al., supra), the human fMLP receptor (Boulay et al., supra), the human C5a receptor (Gerard and Gerard, supra), and/or the receptor described by Murphy and Tiffany, supra.

Identity or homology with respect to a PF4AR is defined herein to be the percentage of amino acid residues in the candidate sequence that are identical with the residues in FIGS. 2, 4 or 5 after aligning the sequences and introducing gaps, if necessary, to achieve the maximum percent homology, and not considering any conservative substitutions as representing residue identity. No N-nor C-terminal extensions, deletions nor insertions shall be construed as reducing identity or homology.

PF4AR qualitative biological activity is defined as any one of (1) immunological cross-reactivity with at least one epitope of a polypeptide set forth in FIGS. 2, 4, or 5; (2) the ability to specifically bind to a member of the PF4 superfamily; or (3) any effector or functional activity of the FIGS. 2, 4 or 5 polypeptides as found in nature, including their ability to bind any ligands other than superfamily members.

Immunologically cross-reactive as used herein means that the candidate polypeptide is capable of competitively inhibiting the binding of a PF4AR to polyclonal antibodies or antisera raised against a PF4AR. Such antibodies and antisera are prepared in conventional fashion by injecting an animal such as a goat or rabbit, for example, subcutaneously with the known native PF4AR in complete Freund's adjuvant, followed by booster intraperitoneal or subcutaneous injection in incomplete Freund's.

Included within the scope of the PF4AR as that term is used herein are polypeptides having the amino acid sequences described in FIGS. 2, 4 or 5, amino acid sequence variants of such amino acid sequences, glycosylation variants of the polypeptides and covalent modifications of the polypeptides. Each of these are described in more detail below.

"Isolated" PF4AR nucleic acid or polypeptide is a PF4AR nucleic acid or polypeptide that is identified and separated from at least one contaminant (nucleic acid or polypeptide respectively) with which it is ordinarily associated in nature, such as from the animal or human source of the PF4AR nucleic acid or polypeptide. In preferred embodiments, the PF4AR will be isolated to pharmaceutically acceptable levels of purity with respect to proteins of its species of origin. In preferred embodiments, PF4AR protein will be purified (1) to greater than 95% by weight of protein as determined by the Lowry method, and most preferably more than 99% by weight, (2) to a degree sufficient to obtain at least 15 residues of N-terminal or internal amino acid sequence by an amino acid sequenator commercially available on the filing date hereof, or (3) to homogeneity by conventional nonreducing SDS-PAGE using Coomassie blue or, preferably, silver stain. Isolated PF4AR includes PF4AR in situ within recombinant cells since, in this instance, at least one component of the PF4AR natural environment will not be present. Isolated PF4AR includes PF4AR from one species in a recombinant cell culture of another species since the receptor in such circumstances will be devoid of source polypeptides. Ordinarily, however, isolated receptor will be prepared by at least one purification step.

Isolated PF4AR nucleic acid includes a nucleic acid that is identified and separated from at least one containment nucleic acid with which it is ordinarily associated in the natural source of the receptor nucleic acid. Isolated PF4AR nucleic acid thus is present in other than in the form or setting in which it is found in nature. However, isolated receptor-encoding nucleic acid includes PF4AR nucleic acid in ordinarily receptor-expressing cells where the nucleic acid is in a chromosomal location different from that of natural cells or is otherwise flanked by a different DNA sequence than that found in nature.

The nucleic acid or polypeptide may be labeled for diagnostic and probe purposes, using a label as described and defined further below in the discussion of diagnostic assays.

PF4AR "nucleic acid" is defined as RNA or DNA containing greater than ten bases that encodes a polypeptide sequence within FIGS. 2, 4 or 5, is complementary to nucleic acid sequence of FIGS. 2, 4 or 5, hybridizes to such nucleic acid and remains stably bound to it under low stringency conditions, or encodes a polypeptide sharing at least 30% sequence identity, preferably at least 75%, and more preferably at least 85%, with the translated amino acid sequence shown in FIGS. 2, 4 or 5 or a fragment thereof. Preferably the DNA which hybridizes to the nucleic acid of FIGS. 2, 4 or 5 contain at least 20, more preferably 40, and more preferably 60 bases. Most preferably, the hybridizing DNA or RNA contains 45 or even more preferably 90 bases. Such hybridizing or complementary nucleic acid, however, is defined further as being novel and unobvious over any prior art nucleic acid including that which encodes, hybridizes under low stringency conditions, or is complementary to nucleic acid encoding rabbit fMLP receptor (Thomas et al., supra), human fMLP receptor or (optionally) the IL-8 receptor of Murphy and Tiffany, supra.

"High stringency conditions" are any of those that (1) employ low ionic strength and high temperature for washing, for example, 0.015M NaCl/0.0015M sodium citrate/0.1% NaDodSO$_4$ at 50° C.; (2) employ during hybridization 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ hybridization with 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. Conditions of low stringency are set forth in Example 2.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice.

The starting plasmids herein are commercially available, are publicly available on an unrestricted basis, or can be constructed from such available plasmids in accord with published procedures. In addition, other equivalent plasmids are known in the art and will be apparent to the ordinary artisan. Methods for restriction enzyme digestion, recovery or isolation of DNA, hybridization analysis, and ligation are conventional and by this time well known to the ordinary artisan.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9: 6103–6114 (1981), and Goeddel et al., *Nucleic Acids Res.*, 8: 4057 (1980).

As used herein, the term "mammal" refers to any animal classified as a mammal, including humans, domestic and farm animals, and zoo, sports, or pet animals, such as dogs, horses, cats, cows, etc. Preferably, the mammal herein is human.

As used herein, the term "treatment" refers to therapy as well as prophylactic (preventative) measures.

As used herein, the term "inflammatory disorders" refers to pathological states resulting in inflammation, typically caused by neutrophil chemotaxis. Examples of such disorders include T cell inflammatory responses such as inflammatory skin diseases including psoriasis; responses associated with inflammatory bowel disease (such as Crohn's disease and ulcerative colitis); adult respiratory distress syndrome; dermatitis; meningitis; encephalitis; uveitic; allergic conditions such as eczema and asthma and other conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, multiple sclerosis. Reynaud's syndrome, autoimmune thyroiditis, experimental autoimmune encephalomyelitis. Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; diseases involving leukocyte diapedesis; CNS inflammatory disorder, multiple organ injury syndrome secondary to septicaemia or trauma; autoimmune haemolytic anemia; myethemia gravis; antigen-antibody complex mediated diseases; inflammations of the lung, including pleurisy, alveolitis, vasculitis, pneumonia, chronic bronchitis, bronchiectasis, and cystic fibrosis; etc. The preferred indications are inflammatory bowel disease such as ulcerative colitis or a chronic lung inflammation.

II. Suitable Methods for Practicing the Invention
1. Preparation of Native PF4AR and Variants
A. Isolation of DNA Encoding PF4AR The DNA encoding of the PF4AR may be obtained from any cDNA library prepared from tissue believed to contain the PF4AR mRNA, generally HL60 or PBL libraries. The PF4AR gene may also be obtained from a genomic library. Libraries are screened with probes designed to identify the gene of interest or the protein encoded by it. The entire cDNA for the IL-8 receptor and two homologous receptors is described. Nucleic acid encoding this family of receptors is readily obtained under low stringency conditions from genomic DNA or neutrophil cDNA libraries using probes having oligonucleotide sequences from the receptor gene sequences of FIGS. 2, 4 or 5. These probes usually will contain about 500 or more bases. Since the probes will hybridize perfectly to the three exemplified DNAs, there is no need to use probe pools containing degenerate sequences. Screening with the probes to identify the FIGS. 2, 4 or 5 receptors is more efficient if performed under conditions of high stringency.

Other PF4ARs other than those in FIGS. 2, 4 or 5 are believed to exist and to contain regions of homology to the exemplified receptors. Thus probes having the sequences of the DNAs in FIGS. 2, 4 or 5 can be used to screen for these receptors as well. The best candidates for probes are long sequences (greater than about 100 bases) that represent sequences that are highly homologous among the three exemplified human receptors. IL-8 receptor cDNA encoding the IL-8 receptor residues 15-34, 78-94, 176-193, 264-282 and 299-312 (and comparable probes from other receptors of the IL-8R family) are useful, particularly in probing for IL-8 receptor DNA. Probes useful for the receptor of FIG. 4 (and isolated proteins characteristic of the FIG. 5 receptor) are represented by sequences comprising residues 1-48, 77-92, 107-137, 156-177, 189-226, 239-257 and 271-315. Homologous probes and residues of the FIG. 4 receptor also are useful, i.e. residues 1-35, 64-78, 94-124, 143-164, 176-197, 219-239 and 251-295. cDNAs comprising cDNA encoding the following regions of the FIGS. 2, 4 or 5 polypeptides are useful in probing for other receptors: 92-106, 57-72, 138-154, 314-329 and 57-154.

In general, one first identifies a cell which is capable of specifically binding or which is activated by a given PF4A, typically by in vitro bioassays and, optionally, by cell binding analysis using the labelled PF4A. Cells identified by this process (and some are already known for individual PF4As) therefore are expressing a receptor for this PF4A. A cDNA library is prepared from such cells and is screened using the receptor probes by procedures that are conventional per se. In this instance, however, it is preferred to use low stringency conditions (such as those in Example 2) and then analyze the resulting positive clones for homology to the FIGS. 2, 4 or 5 receptors. In general, candidate human PF4ARs will exhibit greater than about 30% amino acid sequence homology to the FIGS. 2, 4 or 5 receptors and bear a similar transmembrane loop structure.

Assays are then conducted to confirm that the hybridizing full length genes are the desired PF4AR. The candidate is simply inserted into an expression vector and transformed into a host cell that ordinarily does not bind to the candidate PF4A ligand. Transformants that acquire the ability to bind the ligand thus bear the desired receptor gene. In Example 2, we show that two additional homologous polypeptide sequences representing PR4ARs are identified using IL-8R DNA encoding residues 23-314, although the particular probe is not believed to be critical.

An alternative means to isolate genes encoding additional PF4ARs is to use polymerase chain reaction (PCR) methodology (U.S. Pat. No. 4,683,195; Erlich, ed., *PCR Technology*, 1989) to amplify the target DNA or RNA, e.g. as described in section 14 of Sambrook et al., supra. This method requires the use of oligonucleotide primers that will be expected to hybridize to the PF4AR, and these readily are selected from the receptor cDNAs of FIGS. 2, 4 or 5. Strategies for selection of oligonucleotide primers are described above.

cDNA libraries may be screened from various tissues, preferably mammalian PBL, monocyte, placental, fetal, brain, and carcinoma cell lines in order to obtain DNA encoding the receptors of FIGS. 2, 4 or 5, or homologous receptors. More preferably, human or rabbit placental, fetal, brain, and carcinoma cell line cDNA libraries are screened with labelled oligonucleotide probes.

Another method for obtaining the gene of interest is to chemically synthesize it using one of the methods described in Engels et al., *Agnew. Chem. Int. Ed. Engl.*, 28: 716–734 (1989), specifically incorporated by reference. These methods include triester, phosphite, phosphoramidite and H-phosphonate methods, typically proceeding by oligonucleotide synthesis on solid supports. These methods may be used if the entire amino acid or nucleic acid sequence of the gene is known, or the sequence of the nucleic acid complementary to the coding strand is available. If the desired amino acid sequence is known, one may infer potential nucleic acid sequences using known and preferred coding residues for each amino acid residue.

B. Amino Acid Sequence Variants of the PF4AR

Amino acid sequence variants of the PF4AR are prepared by introducing appropriate nucleotide changes into the PF4AR DNA, or by in vitro synthesis of the desired PF4AR polypeptide. Such variants include, for example, deletions from, or insertions or substitutions of, residues within the amino acid sequence shown for the receptors in FIGS. 2, 4 or 5. Any combination of deletion, insertion, and substitution can be made to arrive at the final construct, provided that the final construct possesses the desired characteristics.

The amino acid changes also may alter post-translational processing of the PF4AR, such as changing the number or position of glycosylation sites or by altering its membrane anchoring characteristics. Excluded from the scope of this invention are PF4AR variants or polypeptide sequences that are not statutorily novel and unobvious over the prior art.

In designing amino acid sequence variants of PF4ARs, the location of the mutation site and the nature of the mutation will depend on the PF4AR characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the PF4AR polypeptide that are preferred locations for mutagenesis is called "alanine scanning mutagenesis" as described by Cunningham and Wells, *Science*, 244: 1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis may be conducted at the target codon or region and the expressed PF4AR variants are screened for the optimal combination of desired activity.

In general, the regions of the PF4AR molecule preferred for alterations are non-hydrophilic regions or regions that are not highly conserved. Such regions are those in which sequences of 5 or more residues are not substantially conserved in the homologous positions in the rabbit fMLP receptor, the human fMLP receptor, the human C5a receptor and the receptors of FIGS. 2, 4 and 5.

PF4AR variants will exhibit at least a biological activity of the parental sequence, for example ligand binding activity or antigenic activity. Antigenically active PF4AR is a polypeptide that binds with an affinity of at least about $10^{-9}$ 1/mole to an antibody raised against a naturally occurring PF4AR sequence. Ordinarily the polypeptide binds with an affinity of at least about $10^{-8}$ 1/mole. Most preferably, the antigenically active PF4AR is a polypeptide that binds to an antibody raised against the receptor in its native conformation. "native conformation" generally meaning the receptor as found in nature which has not been denatured by chaotropic agents, heat or other treatment that substantially modifies the three dimensional structure of the receptor (this can be determined, for example, by migration on nonreducing, nondenaturing sizing gels). Antibody used in determination of antigenic activity is rabbit polyclonal antibody raised by formulating the native non-rabbit receptor in Freund's complete adjuvant, subcutaneously injecting the formulation, and boosting the immune response by intraperitoneal injection of the formulation until the titer of anti-receptor antibody plateaus.

One group of variants are deletion mutants, or fragments of the sequences set forth in FIGS. 2, 4, 5 or other PF4AR. In general, the fragments are those which constitute the extracellular regions of the receptors (these receptors are unlike most in that they are believed to contain a plurality of hydrophobic, transmembrane domains separated by hydrophilic sequences believed to loop into the ectoplasm). Particularly of interest are the N-terminal extracellular region containing acidic amino acid residues. However, any sequence which is capable of raising an antibody that will cross-react with the intact receptor, or which will bind to a member of the PF4 superfamily, is useful. These fragments typically will contain a consecutive sequence of at least about 5 (and ordinarily at least about 10) residues.

Amino acid sequence deletions generally range from about 1 to 30 residues, more preferably about 1 to 10 residues, and typically are contiguous. Deletions may be introduced into regions of low homology among the receptors of FIGS. 2, 4 and 5 to modify the activity of the receptors. Such deletions will be more likely to modify the biological activity of the receptors more significantly than deletions made elsewhere. The number of consecutive deletions will be selected so as to preserve the tertiary structure of the PF4AR in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the PF4AR sequence) may range generally from about 1 to 10 residues, more preferably 1 to 5, most preferably 1 to 3.

Insertional variants of the PF4AR or its extracellular segments include the fusion to the N- or C-terminus of the PF4AR of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published 6 Apr. 1989.

Another group of variants are amino acid substitution variants. These variants have at least one amino acid residue in the PF4AR molecule removed and a different residue inserted in its place. The sites of greatest interest for substitutional mutagenesis include sites identified as the active site(s) of the PF4AR, and sites where the amino acids found in the PF4AR from various species are substantially different in terms of side-chain bulk, charge, and/or hydrophobicity.

Other sites of interest are those in which particular residues of the PF4ARs of FIGS. 2, 4 and 5 are identical. These positions may be important for the biological activity of the PF4AR. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | giu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the PF4AR are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another. Such substituted residues may be introduced into regions of the PF4AR that are homologous with other PF4ARs, or, more preferably, into the non-homologous regions of the molecule.

Any cysteine residues not involved in maintaining the proper conformation of the PF4AR may be substituted, generally with serine, to improve the oxidative stability of the molecule and prevent aberrant crosslinking.

DNA encoding amino acid sequence variants of the PF4AR is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the PF4AR. These techniques may utilize PF4AR nucleic acid (DNA or RNA), or nucleic acid complementary to the PF4AR nucleic acid.

Oligonucleotide-mediated mutagenesis is a preferred method for preparing substitution, deletion, and insertion variants of PF4AR DNA. This technique is well known in the art, for example as described by Adelman et al., *DNA*, 2: 183 (1983). Briefly, the PF4AR DNA is altered by hybridizing an oligonucleotide encoding the desired mutation to a DNA template, where the template is the single-stranded form of a plasmid or bacteriophage containing the unaltered or native DNA sequence of the PF4AR. After hybridization, a DNA polymerase is used to synthesize an entire second complementary strand of the template that will thus incorporate the oligonucleotide primer, and will code for the selected alteration in the PF4AR DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75: 5765 (1978).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the PF4AR, and the other strand (the original template) encodes the native, unaltered sequence of the PF4AR. This heteroduplex molecule is then transformed into a suitable host cell, usually a prokaryote such as *E. coli* JM101. The cells are plated onto agarose plates, and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (DATP), deoxyriboguanosine (dGTP), and deoxyribothymidine (dTTP), is combined with a modified thio-deoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding PF4AR mutants at more than one site may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of the PF4AR. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

Another method for preparing variants, cassette mutagenesis, is based on the technique described by Wells et al., *Gene*, 34: 315 (1985).

C. Insertion of DNA into a Cloning Vehicle

The cDNA or genomic DNA encoding native or variant PF4AR is inserted into a replicable vector for further cloning (amplification of the DNA) or for expression. Many vectors are available, and selection of the appropriate vector will depend on (1) whether it is to be used for DNA amplification or for DNA expression, (2) the size of the DNA to be inserted into the vector, and (3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, a signal sequence may be a component of the vector, or it may be a part of the PF4AR DNA that is inserted into the vector. The native pro PF4AR DNA is directed to the cell surface in our recombinant cells but it does not contain a conventional signal and no N-terminal polypeptide is cleaved during post-translational processing of the polypeptide during membrane insertion of the PF4AR.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the PF4AR DNA. However, the recovery of genomic DNA encoding the PF4AR is more complex than that of an exogenously replicated vector because restriction enzyme digestion is required to excise the PF4AR DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.*, 1: 327 [1982]), mycophenolic acid (Mulligan et al., *Science*, 209: 1422 [1980]) or hygromycin (Sugden et al., *Mol. Cell. Biol.*, 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the PF4AR nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the PF4AR. Amplification is the process by which genes in greater demand for the production of a protein critical for growth are reiterated in tandem within the chromosomes of successive generations of recombinant cells. Increased quantities of the PF4AR are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the PF4AR. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the PF4AR, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965, 199.

A suitable selection gene for use in yeast is the trp1 gene present in the yeast plasmid YRp7. Stinchcomb et al., *Nature*, 282: 39 (1979); Kingsman et al., *Gene*, 7: 141 (1979); or Tschemper et al., *Gene*, 10: 157 (1980). The trp1 gene provides a selection marker for a mutant strain of yeast lacking the ability to grow in tryptophan, for example, ATCC No. 44076 or PEP4-1. Jones, *Genetics*, 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression vectors usually contain a promoter that is recognized by the host organism and is operably linked to the PF4AR nucleic acid. Promoters are untranslated sequences located upstream (5') to the start codon of a structural gene (generally within about 100 to 1000 bp) that control the transcription and translation of a particular nucleic acid sequence, such as the PF4AR, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the PF4AR by removing the promoter from the source DNA by restriction enzyme digestion and inserting the isolated promoter sequence into the vector. Both the native PF4AR promoter sequence and many heterologous promoters may be used to direct amplification and/or expression of the PF4AR DNA. However, heterologous promoters are preferred, as they generally permit greater transcription and higher yields of expressed PF4AR as compared to the native PF4AR promoter.

Promoters suitable for use with prokaryotic hosts include the β-lactamase and lactose promoter systems (Chang et al., *Nature*, 275: 615 [1978]; and Goeddel et al., *Nature*, 281: 544 [1979]), alkaline phosphatase, a tryptophan (trp) promoter system (Goeddel, *Nucleic Acids Res.*, 8: 4057 [1980] and EP 36,776) and hybrid promoters such as the tac promoter (deBoer et al., *Proc. Natl. Acad. Sci. USA*, 80: 21–25 [1983]). However, other known bacterial promoters are suitable. Their nucleotide sequences have been published, thereby enabling a skilled worker operably to ligate them to DNA encoding the PF4AR (Siebenlist et al., *Cell*, 20: 269 [1980]) using linkers or adaptors to supply any required restriction sites. Promoters for use in bacterial systems also generally will contain a Shine-Dalgarno (S.D.) sequence operably linked to the DNA encoding the PF4AR.

Suitable promoting sequences for use with yeast hosts include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; and Holland, *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

PF4AR transcription from vectors in mammalian host cells is controlled by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the PF4AR sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273: 113 (1978); Mulligan and Berg, *Science*, 209: 1422–1427 (1980); Pavlakis et al., *Proc. Natl. Acad. Sci. USA*, 78: 7398–7402 (1981). The immediate early promoter of the human cytomegalovirus is conveniently obtained as a HindIII E restriction fragment. Greenaway et al., *Gene*, 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells, Reyes et al., *Nature*, 297: 598–601 (1982) on expression of human β-interferon cDNA in mouse cells under the control of a thymidine kinase promoter from herpes simplex virus, Canaani and Berg, *Proc. Natl. Acad. Sci. USA*, 79: 5166–5170 (1982) on expression of the human interferon β1 gene in cultured mouse and rabbit cells, and Gorman et al., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the PF4AR of this invention by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., *Proc. Natl. Acad. Sci. USA*, 78: 993 [1981]) and 3' (Lusky et al., *Mol. Cell Bio.*, 3: 1108 [1983]) to the transcription unit, within an intron (Banerji et al., *Cell*, 33: 729 [1983]) as well as within the coding sequence itself (Osborne et al., *Mol. Cell Bio.*, 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5' or 3' to the PF4AR DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the PF4AR. The 3' untranslated regions also include transcription termination sites.

Suitable vectors containing one or more of the above listed components and the desired coding and control sequences are constructed by standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

Particularly useful in the practice of this invention are expression vectors that provide for the transient expression in mammalian cells of DNA encoding the PF4AR. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of the PF4AR that have PF4AR-like activity.

Other methods, vectors, and host cells suitable for adaptation to the synthesis of the PF4AR in recombinant vertebrate cell culture are described in Gething et al., *Nature*, 293: 620–625 (1981); Mantei et al., *Nature*, 281: 40–46 (1979); Levinson et al., EP 117,060; and EP 117,058. A particularly useful plasmid for mammalian cell culture expression of the PF4AR is pRK5 (EP pub. no. 307,247) or pSVI6B (PCT pub. no. WO 91/08291 published 13 Jun. 1991).

D. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcescens*. One preferred *E. coli* cloning host is *E.*

*coli* 294 (ATCC 31,446), although other strains such as *E. coli* B, *E. coli* χ1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for vectors containing PF4AR DNA. *Saccharomyces cerevisiae*, or common baker's yeast, is the most commonly used among lower eukaryotic host microorganisms. However, a number of other genera, species, and strains are commonly available and useful herein, such as *S. pombe* (Beach and Nurse, *Nature*, 290: 140 [1981]), *Kluyveromyces lactis* (Louvencourt et al., *J. Bacteriol.*, 737 [1983]), *yarrowia* (EP 402,226), *Pichia pastoris* (EP 183,070), *Trichoderma reesia* (EP 244,234), *Neurospora crassa* (Case et al., *Proc. Natl. Acad. Sci. USA*, 76: 5259–5263 [1979]), and Aspergillus hosts such as *A. nidulans* (Ballance et al., *Biochem. Biophys. Res. Commun.*, 112: 284–289 [1983]; Tilburn et al., *Gene*, 26: 205–221 [1983]; Yelton et al., *Proc. Natl. Acad. Sci. USA*, 81: 1470–1474 [1984]) and *A. niger* (Kelly and Hynes, *EMBO J.*, 4: 475–479 [1985]).

Suitable host cells for the expression of glycosylated PF4AR polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., *Bio/Technology*, 6: 47–55 (1988); Miller et al., in *Genetic Engineering*, Setlow, J. K. et al., 8: 277–279 (Plenum Publishing, 1986), and Maeda et al., *Nature*, 315: 592–594 (1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the PF4AR DNA. During incubation of the plant cell culture with *A. tumefaciens*, the DNA encoding PF4AR is transferred to the plant cell host such that it is transfected, and will, under appropriate conditions, express the PF4AR DNA. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. See EP 321,196 published 21 Jun. 1989.

However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 (1977); baby hamster kidney cells (BHK, ATCC CCL 10); Chinese hamster ovary cells/ –DHFR (CHO, Urlaub and Chasin, *Proc. Natl. Acad. Sci. USA*, 77: 4216 [1980]); mouse sertoli cells (TM4, Mather, *Biol. Reprod.*, 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 [1982]); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published 29 Jun. 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.*, 130: 946 (1977) and Hsiao et al., *Proc. Natl. Acad. Sci.* (*USA*), 76: 3829 (1979). However, other methods for introducing DNA into cells such as by nuclear injection, electroporation, or by protoplast fusion may also be used.

E. Culturing the Host Cells

Prokaryotic cells used to produce the PF4AR polypeptide of this invention are cultured in suitable media as described generally in Sambrook et al., supra.

The mammalian host cells used to produce the PF4AR of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767,704; 4,657,866;

4,927,762; or 4,560,655; WO 90/03430; WO 87/00195; U.S. Pat. No. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that the PF4AR of this invention may be produced by homologous recombination, or with recombinant production methods utilizing control elements introduced into cells already containing DNA encoding the PF4AR. For example, a powerful promoter/enhancer element, a suppressor, or an exogenous transcription modulatory element is inserted in the genome of the intended host cell in proximity and orientation sufficient to influence the transcription of DNA encoding the desired PF4AR. The control element does not encode the PF4AR of this invention, but the DNA is present in the host cell genome. One next screens for cells making the PF4AR of this invention, or increased or decreased levels of expression, as desired.

F. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77: 5201–5205 [1980]), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/or assay of sample fluids may be either monoclonal or polyclonal, and may be prepared in any mammal. Conveniently, the antibodies may be prepared against a native PF4AR polypeptide or against a synthetic peptide based on the DNA sequences provided herein as described further in Section 4 below.

G. Purification of The PF4AR Polypeptide

The PF4AR is recovered from the culture cells by solubilizing cell membrane in detergent.

When a human PF4AR is expressed in a recombinant cell other than one of human origin, the PF4AR is completely free of proteins or polypeptides of human origin. However, it is necessary to purify the PF4AR from recombinant cell proteins or polypeptides to obtain preparations that are substantially homogeneous as to the PF4AR. As a first step, the cells are centrifuged to separate them from culture medium. The membrane and soluble protein fractions are then separated. The PF4AR may then be purified from the membrane fraction of the culture lysate by solubilization with detergents followed by suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using the appropriate PF4A immobilized on a matrix.

PF4AR variants in which residues have been deleted, inserted or substituted are recovered in the same fashion as the native PF4AR, taking account of any substantial changes in properties occasioned by the variation. For example, preparation of a PF4AR fusion with another protein or polypeptide, e.g. a bacterial or viral antigen, facilitates purification; an immunoaffinity column containing antibody to the antigen can be used to adsorb the fusion. Immunoaffinity columns such as a rabbit polyclonal anti-PF4AR column can be employed to absorb the PF4AR variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native PF4AR may require modification to account for changes in the character of the PF4AR or its variants upon expression in recombinant cell culture.

H. Covalent Modifications of PF4AR Polypeptides

Covalent modifications of PF4AR polypeptides are included within the scope of this invention. Both native PF4ARs and amino acid sequence variants of the PF4AR may be covalently modified. Covalent modifications of the PF4AR, fragments thereof or antibodies thereto are introduced into the molecule by reacting targeted amino acid residues of the PF4AR, fragments thereof, or PF4AR antibody with an organic derivatizing agent that is capable of reacting with selected side chains or the N- or C-terminal residues. Most commonly, PF4AR and its antibodies are covalently bonded to detectable groups used in diagnosis, e.g. enzymes, radio isotopes, spin labels, antigens, fluorescent or chemiluminescent groups and the like.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidazole)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking PF4AR, its fragments or antibodies to a water-insoluble support matrix or surface for use in methods for purifying anti-PF4AR antibodies, and vice versa. Immobilized PF4AR also is useful in screening for the PF4 super-family members to which the receptor binds. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)-dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group.

Another type of covalent modification of the beta-8 polypeptide included within the scope of this invention comprises altering the native glycosylation pattern of the polypeptide. By altering is meant deleting one or more carbohydrate moieties found in the native receptor, and/or adding one or more glycosylation sites that are not present in the native receptor.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used. As noted above, the IL-8 receptor contains 6 putative N-linked glycosylation sites.

Addition of glycosylation sites to the PF4AR polypeptide is conveniently accomplished by altering the amino acid sequence such that it contains one or more of the above-described tri-peptide sequences (for N-linked glycosylation sites). The alteration may also be made by the addition of, or substitution by, one or more serine or threonine residues to the native PF4AR sequence (for O-linked glycosylation sites). For ease, the PF4AR amino acid sequence is preferably altered through changes at the DNA level, particularly by mutating the DNA encoding the PF4AR polypeptide at preselected bases such that codons are generated that will translate into the desired amino acids. The DNA mutation(s) may be made using methods described above under the heading of "Amino Acid Sequence Variants of PF4AR Polypeptide".

Another means of increasing the number of carbohydrate moieties on the PF4AR polypeptide is by chemical or enzymatic coupling of glycosides to the polypeptide. These procedures are advantageous in that they do not require production of the polypeptide in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston (*CRC Crit. Rev. Biochem.*, pp. 259–306 [1981]).

Removal of carbohydrate moieties present on the native PF4AR polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., *Arch. Biochem. Biophys.*, 259: 52 (1987) and by Edge et al., *Anal. Biochem.*, 118: 131 (1981). Enzymatic cleavage of carbohydrate moieties on polypeptides can be achieved by the use of a variety of endo- and exoglycosidases as described by Thotakura et al., *Meth. Enzymol.*, 138: 350 (1987).

Glycosylation at potential glycosylation sites may be prevented by the use of the compound tunicamycin as described by Duskin et al., *J. Biol. Chem.*, 257: 3105 (1982). Tunicamycin blocks the formation of protein-N-glycoside linkages.

The PF4AR also may be entrapped in microcapsules prepared, for example, by coacervation techniques or by interfacial polymerization (for example, hydroxymethylcellulose or gelatin-microcapsules and poly-|methylmethacylate| microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Osol, A., Ed., (1980).

PF4AR preparations are also useful in generating antibodies, for use as standards in assays for the PF4AR (e.g. by labeling the PF4AR for use as a standard in a radioimmunoassay, enzyme-linked immunoassay, or radioreceptor assay), in affinity purification techniques, and in competitive-type receptor binding assays when labeled with radioiodine, enzymes, fluorophores, spin labels, and the like.

Since it is often difficult to predict in advance the characteristics of a variant PF4AR, it will be appreciated that some screening of the recovered variant will be needed to select the optimal variant. For example, a change in the immunological character of the PF4AR molecule, such as affinity for a given antibody, is measured by a competitive-type immunoassay. The variant is assayed for changes in the suppression or enhancement of its activity by comparison to the activity observed for native PF4AR in the same assay. Other potential modifications of protein or polypeptide properties such as redox or thermal stability, hydrophobicity, susceptibility to proteolytic degradation, or the tendency to aggregate with carriers or into multimers are assayed by methods well known in the art.

3. Therapeutic Compositions and Administration of PF4AR

Therapeutic formulations of PF4AR (including its PF4AR binding fragments) or antibodies thereto are prepared for storage by mixing PF4AR having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The PF4AR, or antibody to be used for in vivo administration must be sterile. This is readily accomplished by filtration through sterile filtration membranes, prior to or following lyophilization and reconstitution. The PF4AR ordinarily will be stored in lyophilized form or in solution.

Therapeutic PF4AR or antibody compositions generally are placed into a container having a sterile access port, for example, an intravenous solution bag or vial having a stopper pierceable by a hypodermic injection needle.

The route of PF4AR or antibody administration is in accord with known methods, e.g. injection or infusion by intravenous, intraperitoneal, intracerebral, intramuscular, intraocular, intraarterial, or intralesional routes, or by sustained release systems as noted below. Preferably the antibody is given systemically.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers*, 22: 547–556 [1983]), poly (2-hydroxyethyl-methacrylate) (Langer et al., *J. Biomed. Mater. Res.*, 15: 167–277 [1981] and Langer, *Chem. Tech.*, 12: 98–105 [1982]), ethylene vinyl acetate (Langer et al., supra) or poly-D-(−)-3-hydroxybutyric acid (EP 133,988). Sustained-release PF4AR or antibody compositions also include liposomally entrapped PF4AR or antibody. Liposomes containing PF4AR or antibody are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal PF4AR or antibody therapy.

An "effective amount" of PF4AR or antibody to be employed therapeutically will depend, for example, upon the therapeutic objectives, the route of administration, the type of PF4AR polypeptide or antibody employed, and the condition of the patient. Accordingly, it will be necessary for the therapist to titer the dosage and modify the route of administration as required to obtain the optimal therapeutic effect. Typically, the clinician will administer the PF4AR or antibody until a dosage is reached that achieves the desired effect. The progress of this therapy is easily monitored by conventional assays.

In the treatment and prevention of an inflammatory disorder by a PF4AR antibody, particularly an IL-8 receptor antibody, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "therapeutically effective amount" of antibody to be administered will be governed by such considerations, and is the minimum amount necessary to prevent, ameliorate, or treat the inflammatory disorder, including treating chronic respiratory diseases and reducing inflammatory responses. Such amount is preferably below the amount that is toxic to the host or renders the host significantly more susceptible to infections.

As a general proposition, the initial pharmaceutically effective amount of the antibody administered parenterally per dose will be in the range of about 0.1 to 50 mg/kg of patient body weight per day, with the typical initial range of antibody used being 0.3 to 20 mg/kg/day, more preferably 0.3 to 15 mg/kg/day.

As noted above, however, these suggested amounts of antibody are subject to a great deal of therapeutic discretion. The key factor in selecting an appropriate dose and scheduling is the result obtained, as indicated above.

The antibody need not be, but is optionally formulated with one or more agents currently used to prevent or treat the inflammatory disorder in question. For example, in rheumatoid arthritis, the antibody may be given in conjunction with a glucocorticosteroid. In addition, T cell receptor peptide therapy is suitably an adjunct therapy to prevent clinical signs of autoimmune encephalomyelitis. Offner et al., supra. The effective amount of such other agents depends on the amount of PF4AR antibody present in the formulation, the type of disorder or treatment, and other factors discussed above. These are generally used in the same dosages and with administration routes as used hereinbefore or about from 1 to 99% of the heretofore employed dosages.

4. PF4AR Antibody Preparation

Polyclonal antibodies to the PF4AR generally are raised in animals by multiple subcutaneous (sc) or intraperitoneal (ip) injections of the PF4AR and an adjuvant. Immunization with recombinant cells transformed with the PF4AR (e.g., 293, mouse, or CHO cells transformed with huPF4AR) may be satisfactory, or it may be useful to separate the PF4AR and conjugate it or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals ordinarily are immunized against the transfected cells, or immunogenic conjugates, derivatives, or peptides every other week. 7 to 14 days after the immunization the animals are bled and the serum is assayed for anti-PF4AR titer. Preferably, the animal is boosted with the conjugate of the same PF4AR, but conjugated to a different protein and/or through a different crosslinking agent. Conjugates also can be made in recombinant cell culture as protein fusions. Also, aggregating agents such as alum are used to enhance the immune response. Less preferably, the animals are immunized by combining 1 mg or 1 µg of PF4AR in Freund's complete adjuvant and injecting the solution intradermally at multiple sites. One month later the animals are boosted with ⅕ to ⅒ the original amount of conjugate in Freund's complete adjuvant by subcutaneous injection at multiple sites. 7 to 14 days later the animals are bled and the serum is assayed for anti-PF4AR titer. Animals are boosted until the titer plateaus.

Another option is to employ combinatorial variable domain libraries and screening methods to identify the desired anti-PF4AR antibodies.

Monoclonal antibodies are prepared by recovering spleen cells from immunized animals and immortalizing the cells in conventional fashion, e.g. by fusion with myeloma cells or by Epstein-Barr (EB) virus transformation and screening for clones expressing the desired antibody.

The monoclonal antibody preferably is specific for each target PF4AR polypeptide, and will not cross-react with rabbit fMLP receptor (Thomas et al., J. Biol. Chem., supra), human fMLP receptor, human C5a receptor the low affinity IL-8 receptor, or other members of the PF4AR family. Antibodies specific for the receptor of FIGS. 2, 4 or 5 are preferred. The antibody is selected to be either agonistic, antagonistic, or to have no effect on the activity of a PF4 super-family member in binding to or activating the receptor.

Murphy and Tiffany, supra, describe a receptor having a high degree of homology to the receptor of FIG. 2. Murphy and Tiffany characterized their receptor in recombinant oocytes as being a receptor for IL-8 and having capability to bind MGSA, thus suggesting that it plays a minor role in IL-8 and MGSA biological activity in vivo. The studies herein, however, have shown that the Murphy and Tiffany receptor exhibits IL-8 affinity as high or higher than the receptor of FIG. 2 and that as well it shows high affinity (about 1–10 nM) for MGSA. Thus, antagonism of the IL-8 and/or MGSA response of lymphoid cells will likely require that both receptors be inhibited or blocked. For example, one should select an IL-8 antagonist antibody that binds to an epitope of the FIG. 2 receptor that is shared by the Murphy and Tiffany receptor. This could be readily accomplished by routine screening methods. For example, the candidate antibodies can be assayed for their ability to compete against labelled IL-8 for binding to cells bearing the FIG. 2 receptor, and then the same study conducted with cells bearing the Murphy and Tiffany receptor. Antibodies that inhibit IL-8 activation or binding to both cells are then selected as therapeutic candidates. On the other hand, antibodies that can discriminate between the FIG. 2 and Murphy and Tiffany receptors and bind only to one or the other are useful in diagnosis. The receptor of FIG. 2 binds MGSA poorly, in contrast to the Murphy and Tiffany receptor.

5. Uses of PF4AR its nucleic acid and its Antibodies

The nucleic acid encoding the PF4AR may be used as a diagnostic for tissue specific typing. For example, such procedures as in situ hybridization, and northern and Southern blotting, and PCR analysis may be used to determine whether DNA and/or RNA encoding the PF4AR are present in the cell type(s) being evaluated. These receptors typically are diagnostic of PBL or monocytic cells.

Isolated PF4AR polypeptide may be used in quantitative diagnostic assays as a standard or control against which samples e.g. from PBL or monocytic cells, containing unknown quantities of PF4AR may be compared. Recombinant cells which express the IL-8 receptor can be used in assays for PF4A ligands in the same fashion as for example neutrophils are used in IL-8 assays. The PF4AR polypeptides, fragments or cells (as such, or derivatized) also can be used as immunogens in the production of antibodies to PF4AR, for the purification of such antibodies from ascites or recombinant cell culture media or for use as competitive anatagonists for superfamily ligands, e.g. IL-8.

The PF4AR are useful in screening for amino acid sequence or other variants of PF4 superfamily members. For example, a bank of candidate IL-8 amino acid sequence variants are prepared by site directed mutagenesis. These are incubated in competition with labelled native IL-8 for cells bearing the IL-8 receptor of FIG. 2 in order identify agonist or antagonist IL-8 variants. Binding or cell activation are suitable assay endpoints. Alternatively, the receptor is recovered in cell-free form and binding of IL-8 and candidate variants assayed.

PF4AR antibodies are useful in diagnostic assays for PF4AR expression in specific cells or tissues wherein the antibodies are labeled in the same fashion as the PF4AR described above and/or are immobilized on an insoluble matrix. PF4AR antibodies also are useful for the affinity purification of the PF4AR from recombinant cell culture or natural sources. The PF4AR antibodies that do not detectably cross-react with other PF4ARs can be used to purify each PF4AR free from other homologous receptors. PF4AR antibodies that are PF4 antagonists are useful as anti-inflammatory agents or in the treatment of other PF4 superfamily-mediated disorders.

Suitable diagnostic assays for the PF4AR and its antibodies are well known per se. Such assays include competitive and sandwich assays, and steric inhibition assays. Competitive and sandwich methods employ a phase-separation step as an integral part of the method while steric inhibition assays are conducted in a single reaction mixture. Fundamentally, the same procedures are used for the assay of the PF4AR and for substances that bind the PF4AR, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for the PF4AR or its antibodies all use one or more of the following reagents: labeled analyte analogue, immobilized analyte analogue, labeled binding partner, immobilized binding partner and steric conjugates. The labeled reagents also are known as "tracers."

The label used (and this is also useful to label PF4AR nucleic acid for use as a probe) is any detectable functionality that does not interfere with the binding of analyte and its binding partner. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. Nos. 3,940,475 (fluorimetry) and 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); and Nygren, *J. Histochem. and Cytochem.*, 30: 407–412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y. York. 1981), pp. 147–166. Such binding methods are suitable for use with PF4AR or its antibodies, all of which are proteinaceous.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, the PF4AR or its immunologically active fragments are conjugated with a bifunctional organic bridge to an enzyme such as peroxidase. Conjugates are selected for use with anti-PF4AR so that binding of the anti-PF4AR inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore. Sandwich assays particularly are useful for the determination of PF4AR or PF4AR antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-PF4AR monoclonal antibody as one antibody and a polyclonal anti-PF4AR antibody as the other is useful in testing samples for PF4AR activity.

The foregoing are merely exemplary diagnostic assays for PF4AR and antibodies. Other methods now or hereafter developed for the determination of these analytes are included within the scope hereof, including the bioassays described above.

The polypeptides set forth in FIGS. 4 and 5 are believed to represent receptors for different and as yet undetermined members of the PF4 superfamily (which includes both the C-C and CXC subfamilies). Like the IL-8 receptor of FIG. 2 they are members of the G-protein-coupled superfamily and bear greater similarity to the IL-8 receptor than other receptors. In preliminary experiments, recombinant cells bearing these receptors do not respond to Rantes, MCP1, IL-8 or MGSA, although they may ultimately be shown to bind other members of the PF4 superfamily or presently unknown ligands. However, whether or not the FIGS. 4 or 5 polypeptides bind to members of the PF4 superfamily, the polypeptides are useful for preparing antibodies for diagnostic use in determining the tissue distribution of the receptors and thus as an immunohistochemical diagnostic for such tissues, in particular as a diagnostic for monocytic cells or PBLs since it is known that such cells express the receptors of FIGS. 4 and 5. Of course, once the PF4 superfamily members are identified which bind to these receptors then the receptors can be used to diagnose the presence of the identified members or for their purification in specific affinity procedures. The DNA in FIGS. 4 and 5 also is useful in diagnostics for the presence of DNA or RNA encoding the IL-8 receptor when low stringency conditions are employed.

All references cited in this specification are expressly incorporated by reference.

The following examples are offered by way of illustration and not by way of limitation.

EXAMPLE 1

To obtain the clone pRK5B.il8r1.1, a cDNA (Gubler and Hoffman, *Gene*, 25: 263–269 [1983]) library of 1,000,000 clones was constructed from human neutrophil mRNA (Chirgwin et al., *Biochem.*, 18: 5294–5299 [1979]) in the vector pRK5B using BstXI linkers. The cDNA is produced in blunted form. Hemi-kinase bstXI linkers are ligated to the CDNA, and the linkers ligated into the PRK5B vector that had been bstXI digested, phosphatased, and the long vector fragment isolated. PRK5B is a derivative of PRK5 (EP 307,247) that contains a cytomegalovirus promoter followed by a 5' intron, bstXI cloning site, and an SV40 early polyadenylation signal, although it will be understood that any mammalian cell expression vector will be satisfactory. 58 pools of 2500 clones each were transfected into COS-7 cells by electroporation (Gearing et al., supra) of 20 µg of DNA into 3,750,000 cells After 2 days of growth on 150-mm dishes in medium (50:50::Ham's F12:DMEM) containing 10% fetal calf serum, $^{125}$I-IL-8 binding was performed. Purified human 72 amino acid IL-8 made in *E. coli* (Hébert et al., *J. Immunology*, 145: 3033–3040 [1990]) was labeled by the lactoperoxidase method (Morrison and Bayse, *Biochem.*, 9: 2995–3000 [1970]) to about 1100 Ci/mmol and was at least 85% bindable. Dishes were rinsed twice with phosphate-buffered saline, and binding was performed with 8 ml per dish of growth medium containing 2.5% fetal calf serum and about 0.5 nM $^{125}$I-IL-8. After 2 hr at 37° C., the plates were rinsed three times with phosphate-buffered saline, the bottoms cut out (Pacholczyk et al., *BioTechniques*, 9: 556–558 [1990]), and autoradiographed. Each positive pool of 2500 cDNA clones was subsequently partitioned into pools of 800 clones, and each of these was transfected and assayed. Each positive pool in turn was subdivided through pools of 185, 30 and finally a single clone(s) until single positive clones were identified to obtain the pure isolate. Since only a portion of each pool was used for transfection it was unnecessary to rescue clones from transformants.

Binding competition was performed with electroporated COS-7 cells after 1 day of expression in 6-well dishes (about 175,000 cells/dish). Binding was performed with radioiodinated wild type IL-8 in binding medium $Ca^{2+}$ and $Mg^{2+}$-free Hanks buffered with 25 nM Hepes and supplemented with 0.5% bovine serum albumin [BSA]) at 4° C. for about 2 hr. Wells were then washed, the cells harvested with trypsin, and counted. No specific binding was found in parallel wells containing cells transfected with DNA from the vector pRK5B. Neutrophil binding was performed as described (Pacholczyk et al., supra) but for 2 hr at 4° C.

EXAMPLE 2

Existing λgt10 cDNA libraries from the human cell line, HL60, and from human peripheral blood lymphocytes were screened at low stringency with a probe from the coding region of the cloned high-affinity human IL-8 receptor (FIG. 2). The probe was the 874 bp PstI/NcoI fragment of the receptor containing the coding region for amino acids 23-314. Hybridization was in 20% formamide, 4×SSC, 50 mM sodium phosphate buffer, pH 7, 0.2 g/l sonicated salmon sperm DNA, 5×Denhardts, 10% dextran sulfate, at 42° C. with a wash at 1×SSC, 0.1% SDS at 50° C. A number of duplicate spots of varying intensity (about 60) were picked, plaque purified, subcloned into plasmid vectors, and sequenced. Nucleic acid sequencing began with the selection of spots of greatest intensity. Sufficient sequence was obtained for a given spot (phage) to determine whether or not evidence of structural or sequence homology with the IL-8 receptor existed. If it did, then the remainder of the gene was obtained (if necessary) and sequenced in its entirety.

To avoid sequences all hybridizing clone the sequence was then used to probe the parental collection of IL-8 receptor DNA hybridizing clones under high stringency conditions in order to identify and discard other spots containing the same hybridizing gene. This technique was highly effective in reducing the sequencing burden. For example, one clone was represented by about one third of the initial 60 clones, and on this result alone the negative screen was able to reduce considering the work involved in sequencing the clones.

From this screen, two new gene sequences were found that are clearly related to the IL-8 receptor. The coding region for one new gene was split between two clones (8rr.20 and 8rr.15). The combined sequence of this gene (8rr.20.15) is shown in FIG. 4. The complete coding region for the second gene is found on clone 8rr.9 (FIG. 5). The predicted amino acid sequence of 8rr.20.15 is 34% identical with both the high and low affinity IL-8 receptor sequences. The sequence of 8rr.9 is 36% and 38% identical with the high and low affinity IL-8 receptor sequences, respectively (Holmes et al., *Science*, 253: 1278 [1991] and Murphy and Tiffany, supra). The amino acid sequence of 8rr.20.15 and 8rr.9 are 31% identical. Use of this probe under low stringency conditions did not produce detectable hybridization to the fMLP receptor genes that were expected to be found in these libraries.

EXAMPLE 3

Monoclonal antibodies to IL-8 type A receptor were generated by immunizing mice with synthetic peptides corresponding to various extracellular domains of IL8R-A or with stably transfected cells expressing IL8R-A, respectively. Blocking and non-blocking monoclonal antibodies were identified and their binding sites were mapped to the N-terminal region of IL8R-A. Details are provided below:
Experimental Protocol Recombinant human IL-8 (rHuIL-8) was produced in *E. coli* and purified as described in Hébert et al., supra.

For generating IL8R-A-bearing cells, human fetal kidney 293 cells were co-transfected with pRK5B.il8r1.1 (Holmes et al., supra) or pRK5.8rr27-1.1 (Lee et al., *J. Biol. Chem.*, 267: 16283–16287 [1992]) and pSVENeoBal6 (Seeburg et al., *Nature*, 312: 71–75 [1984]) plasmids in a 10:1 molar ratio, using a $CaPO_4$ precipitation method as described in Gorman in *DNA Cloning: A Practical Approach*, ed., Glover, D. M. (IRL: Oxford, 1984), Vol. 2, pp. 143–165. Transfected cells were selected in F12/DMEM (50:50) media containing 10% containing 10% fetal calf serum (FCS), 2 mM L-glutamine, 100 µg/ml penicillin, and 100 µg/ml streptomycin. Forty G418-resistant clonal lines were isolated from the pRK5B.il8r1.1 transfection. The IL8R-A-bearing transfected cells were selected by their ability to bind to $^{125}$I-IL-8, and clone 293-71 was used for further study. Thirty G418-resistant clonal lines were isolated from the pRK5.8rr.27-1.1 transfection. After the $^{125}$I-IL-8 binding experiment, clone 36 was selected for further study.

Mutants were prepared by the method of Kunkel, *Proc. Natl. Acad. Sci. USA*, 82: 488 (1985) using the dut- ung- strain of *E. coli* CJ236 and a pUC-derived vector containing a cDNA insert coding for the IL-8 receptor A: pRK5B.IL-8r1.1. Holmes et al., supra. After verification of the mutant DNA sequence with the Sequenase™ version 2.0 kit (U.S. Biochemical Corp.), the mutated plasmid preparations were purified with the Qiagen™ plasmid maxi kit (Qiagen Inc., Chatsworth, Calif.) and used to transfect 293 cells by the calcium phosphate precipitate method of Gorman, supra. The cell cultures were incubated for seven hours in the presence of mutant or wild-type DNA precipitate (10 µg DNA/100 mm dish). The precipitate was then removed and the cells were cultured for an additional 17 hours prior to fluorescence-activated cell sorter (FACS) analysis.

Peptides were synthesized via solid-phase methodology (Barany and Merrifield, in "the peptides," 2: 1–284, Gross and Meienhofer, eds. [Academic Press: New York, 1980]) on either an ABI model 430 peptide synthesizer using tert-butyloxycarbonyl (t-BOC) chemistry or a Milligen model 9050 and ABI model 431 peptide synthesizer using fluorenylmethyloxycarbonyl (FMOC) chemistry. Crude peptides were purified by high-pressure liquid chromatography (HPLC) and analyzed via mass spectrometry. Peptides were conjugated to soybean trypsin inhibitor using m-maleimidobenzoyl-N-hydroxysulfosuccinimide ester (Sulfo-MBS) (Pierce Co., Rockford, Ill.).

BALB/c mice were immunized intraperitoneally with 10 µg of synthetic peptides covering various portions of extracellular domains of IL8R-A conjugated to horse serum albumin or $10^6$ cells/100 µl of 293-71 transfected cells, resuspended in MPL/TDM (Ribi Immunochem. Research Inc., Hamilton, Mont.) and boosted nine times with the same amount of peptides or 16 times with transfected cells. Three days after the final boost with the antigen, spleen cells were fused with mouse myeloma P3X63Ag8U.1 (Yelton et al., *Curr. Top. Microbiol. Immunol.*, 81: 1–7 [1978]), a non-secreting clone of the myeloma P3X63Ag8 (Kohler and Milstein, *Nature*, 256: 495 [1975]) using 35% polyethylene glycol as described by Laskov et al., *Cell. Immunol.*, 55: 251–264 (1980). Ten days after the fusion, culture supernatants were screened for the presence of monoclonal antibodies to IL8R-A by an ELISA or FACS.

Nunc™ brand 96-well immunoplates (Flow Lab, McLean, Va.) were coated with 50 µl/well of 2 µg/mL IL8R-A synthetic peptide in phosphate buffered saline (PBS) overnight at 4° C. The remaining steps were carried out at room temperature as described by Kim et al., *J. Imm. Methods.*, 156: 9 (1992). The isotypes of monoclonal antibodies were determined by coating the plates with IL8R-A peptides overnight, blocked with 0.2% BSA, incubated with culture supernatants, followed by the addition of a predetermined amount of isotype-specific alkaline phosphatase-conjugated goat anti-mouse Ig (Fisher Biotech, Pittsburgh, Pa.). The level of conjugated antibodies that bound to the plate was determined by the addition of p-nitrophenyl phosphate substrate in carbonate buffer containing 1 mM of $MgCl_2$ (Sigma 104 phosphate substrate, Sigma, St. Louis, Mo.). The color reaction was measured at 405 nm with an ELISA plate reader (Titertrek multiscan, Flow Lab, McLean, Va.).

Human neutrophils were prepared by using Mono-Poly Resolving medium (M-PRM) (Flow Lab, McLean, Va.) according to the vendor's direction. Neutrophils or transfected cells were washed twice in the cell sorter buffer (CSB, PBS containing 1% FCS and 0.02% $NaN_3$) at 300×g for 5 minutes. Twenty-five µl of cells ($4 \times 10^6$ cells/ml) were added into a 96-well U-bottom microtiter plate, mixed with 100 µl of culture supernatant or purified monoclonal antibodies, and incubated for 30 min. on ice. After washing, cells were incubated with 100 µl of FITC-conjugated goat-anti-mouse IgG antibodies for 30 min. at 4° C. Cells were washed twice in CSB and resuspended in 150 µl of CSB and analyzed by a FCAScan™ assay (Becton-Dickinson).

The affinity of the monoclonal antibodies was determined by competitive inhibition of the binding of $^{125}$I-monoclonal antibody to 293-71-transfected cells with various concentrations of unlabeled monoclonal antibodies. $^{125}$I-monoclonal antibodies were prepared by using chloramine-T as described by Lee et al., supra. The specific activities of monoclonal antibodies 6C8, 6E9, 2A4, and 9H1 were 0.68 Ci/M, 0.74 Ci/M, 0.814 Ci/M, and 0.922 Ci/M, respectively. Fifty µl of 293-17 ($4 \times 10^6$ cells/ml) resuspended in Hank's buffered saline solution (HBSS) containing 0.5% BSA, were briefly incubated with 100 µl of a fixed concentration of $^{125}$I-monoclonal antibody plus 50 µl of various concentrations of unlabeled monoclonal antibody for one hour at 4° C. The unbound $^{125}$I-monoclonal antibody was removed by centrifugation of the mixture over 0.5 ml of PBS containing 20% sucrose and 0.5% BSA at 1,500 rpm for five minutes. The $^{125}$I-monoclonal antibody bound to the cell pellet was determined using a gamma counter. The affinity of each monoclonal antibody was determined by using Scatplot™ analysis. Munson and Rodbard, *Anal. Biochem.*, 107: 220 (1980).

The blocking ability of the monoclonal antibodies was determined by measuring their effects on the interaction of IL-8 with IL8R-A. Fifty µl of human neutrophils or transfected cells ($4 \times 10^6$ cells/ml) resuspended in the HBSS medium containing 0.5% BSA and 25 mM HEPES buffer were incubated with 50 μl of monoclonal antibodies plus various concentrations of MGSA (0–0.5 nM) for one hour at 4° C. Cells were washed twice in the HBSS medium and resuspended to be 1×10⁶ cells/ml. One hundred μl of cells were incubated with 100 μl of $^{125}$I-IL-8 (1 Ci/M) for one hour at 4° C. and the unbound $^{125}$I-IL-8 was removed using 20% sucrose as described above. The $^{125}$I-IL-8 bound to the cell pellets was counted using a gamma counter.

Results

General Characteristics of the antibodies

For generation of monoclonal antibodies to IL8R-A, mice were immunized either with synthetic peptides corresponding to various extracellular domains of IL8R-A or with stably transfected cells expressing IL8R-A.

Figure 6:
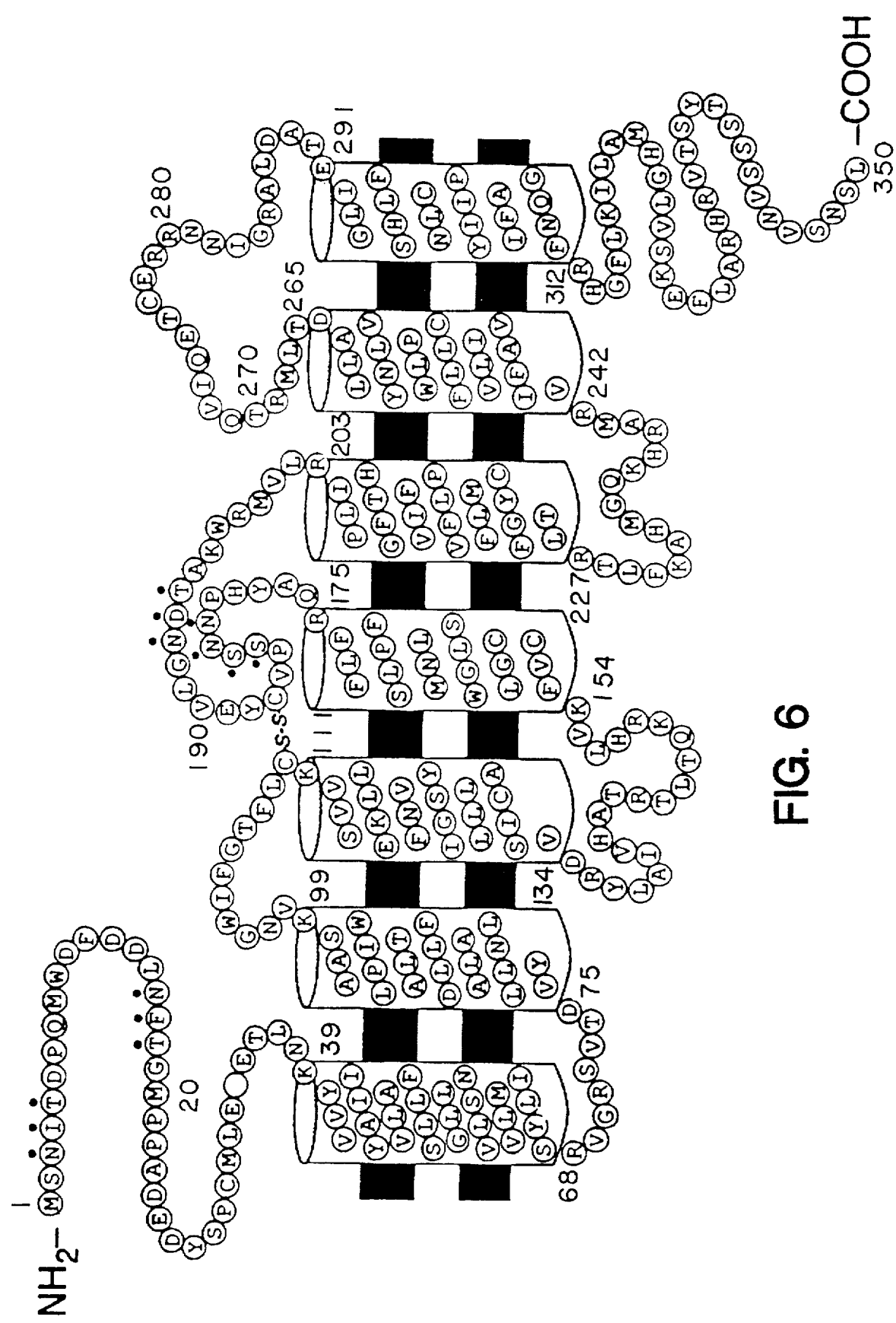
FIG. 6 depicts the structure of the human IL-8 receptor A. 0: glycosylation site. Synthetic peptides covering the extracellular domain of the IL8R-A receptor were made to cover amino acids 2-19, 12-31, 99-110, 176-187, 187-203, 265-277, and 277-291.
Figure 7A:
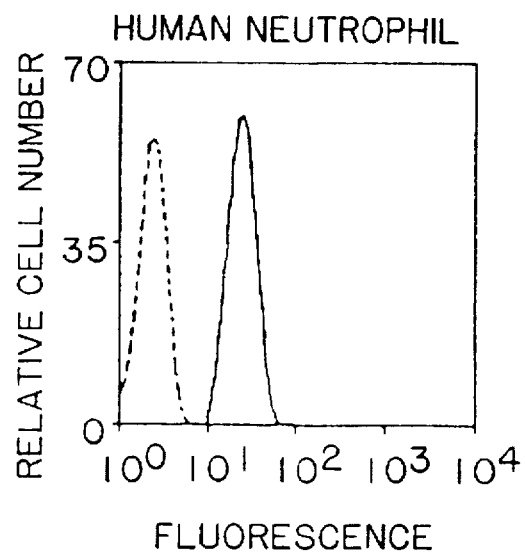
FIGS. 7A, 7B, 7C, and 7D disclose the binding of monoclonal antibody 2A4 to transfected 293 cells expressing IL8R-A (293-71) (FIG. 7C), transfected 293 cells expressing IL8R-B (29-27) (FIG. 7B), untransfected 293 cells (FIG. 7D), and human neutrophils (FIG. 7A). The solid black line is the Mab 2A4 plus F-GαmIg and the dashed line is no MAb plus F-GαmIg (control).
Figure 7B:
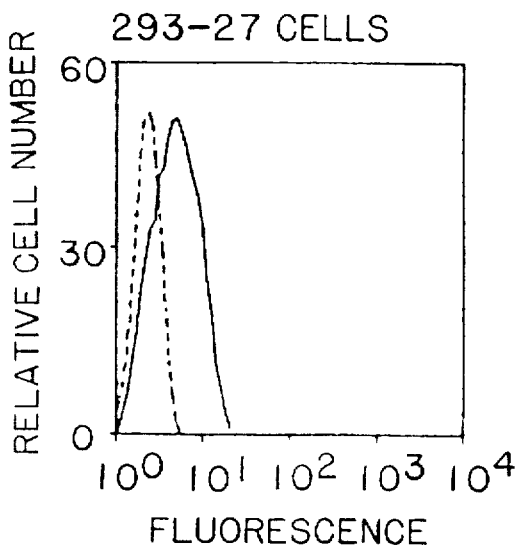
Figure 7C:
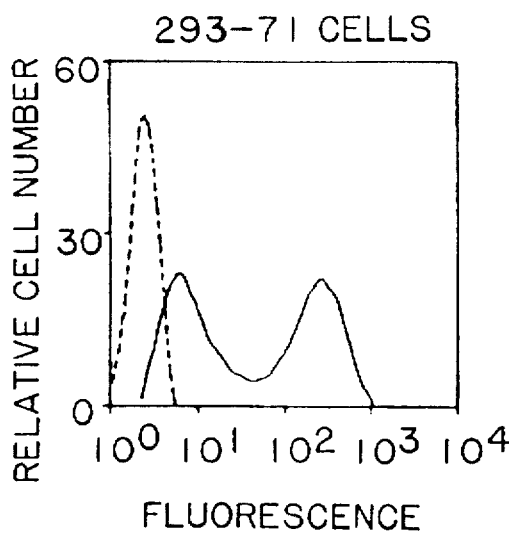
Figure 7D:
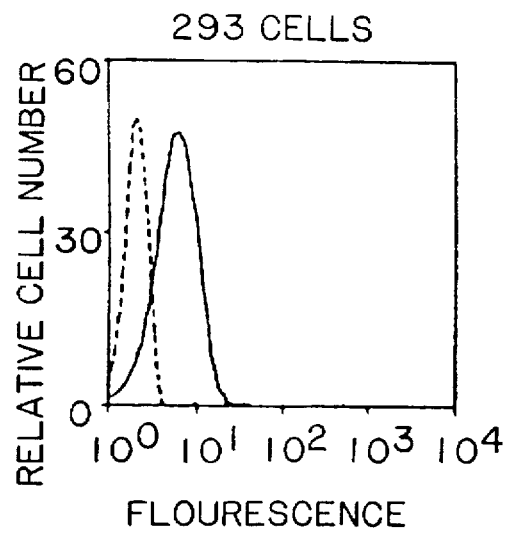

For the first approach, eight peptides were synthesized covering the extracellular domains of IL8R-A, residues 2–19 and 12–31 located within the N-terminal portion of IL8R-A, 99–110 within the first loop, 176–186 and 187–203 within the second loop, and 265–277 and 277–291 within the third loop as shown in FIG. 6. All of these peptides induced high-titer antibodies to each peptide in mice. However, only peptide 2-19 produced polyclonal antibodies that were able to recognize human neutrophils as well as 293-71-transfected cells expressing IL8R-A. The mice immunized with peptide 2-19 were used to generate 36 hybridomas secreting monoclonal antibodies to peptide 2-19. Only two of these monoclonal antibodies (4C8 and 6E9) were able to recognize IL8R-A on 293-transfected cells and were selected for further characterization.

In a second approach, mice were immunized with 293-71 cells producing IL8R-A (293-71). Positive antibody titers were detected only after the 16th immunization. These mice were used to obtain more than 60 positive hybridomas that secreted monoclonal antibodies recognizing IL8R-A on 293-71 cells, as determined by FACS. Two out of 60 monoclonal antibodies, 2A4 and 9H1, were able to inhibit the binding of $^{125}$I-IL-8 to its receptors and were chosen for further evaluation.

These four hybridomas secrete IgGI immunoglobulin isotype (Table 2). Monoclonal antibodies 2A4 and 9H1, generated using transfected cells, have higher affinities than monoclonal antibodies 4C8 and 6E9, generated using peptides (Table 2). All four monoclonal antibodies were able to bind to human neutrophils and 293-71-transfected cells but not to 293 parent cells, as determined by FACS analysis (FIG. 7). Thus, it was concluded that all these monoclonal antibodies were capable of recognizing native IL8R-A.

TABLE 2

| Mab | Immunogen | Isotype | FACS Analysis | | K d |
|-----|-----------|---------|---------|------------|------|
| | | | 293-71 | Neutrophil | (nM) |
| 4C8 | Peptide 2–19 | IgG1 | + | + | 3.26 |
| 6E9 | Peptide 2–19 | IgG1 | + | + | 17.26 |
| 2A4 | 293-71 | IgG1 | + | + | 0.44 |
| 9H1 | 293-71 | IgG1 | + | + | 0.088 |

Cross reactivities to other related receptors

It has been shown that IL-8 specific receptor, IL8R-A, shares 77% amino acid identity with IL8R-B, the common IL-8 /MGSA receptor. For determining whether monoclonal antibodies generated to IL8R-A could recognize IL8R-B, 293 cells transfected with IL8R-B were stained and analyzed by FACS (FIG. 7). All four monoclonal antibodies stained the IL8R-A 293-transfected cells, but not the IL8R-B-transfected 293 cells. The inability of these monoclonal antibodies to bind to 293 cells expressing IL8R-B was not due to the lack of receptor expression, since the same level of $^{125}$I-IL-8 was bound to IL8R-A expressing transfected cells, as well as to the IL8R-B expressing transfected cells.

Inhibition of IL-8 binding to IL8R-A

The effect of the monoclonal antibodies on the binding of $^{125}$I-IL-8 to the 293-71-transfected cells expressing IL8R-A (FIG. 8) was investigated. Monoclonal antibodies 2A4 and 9H1 could completely block the $^{125}$I-IL-8 binding to the 293-71 cells, whereas monoclonal antibodies 4C8 and 6E9 showed very minimal effect.

Figure 8A:
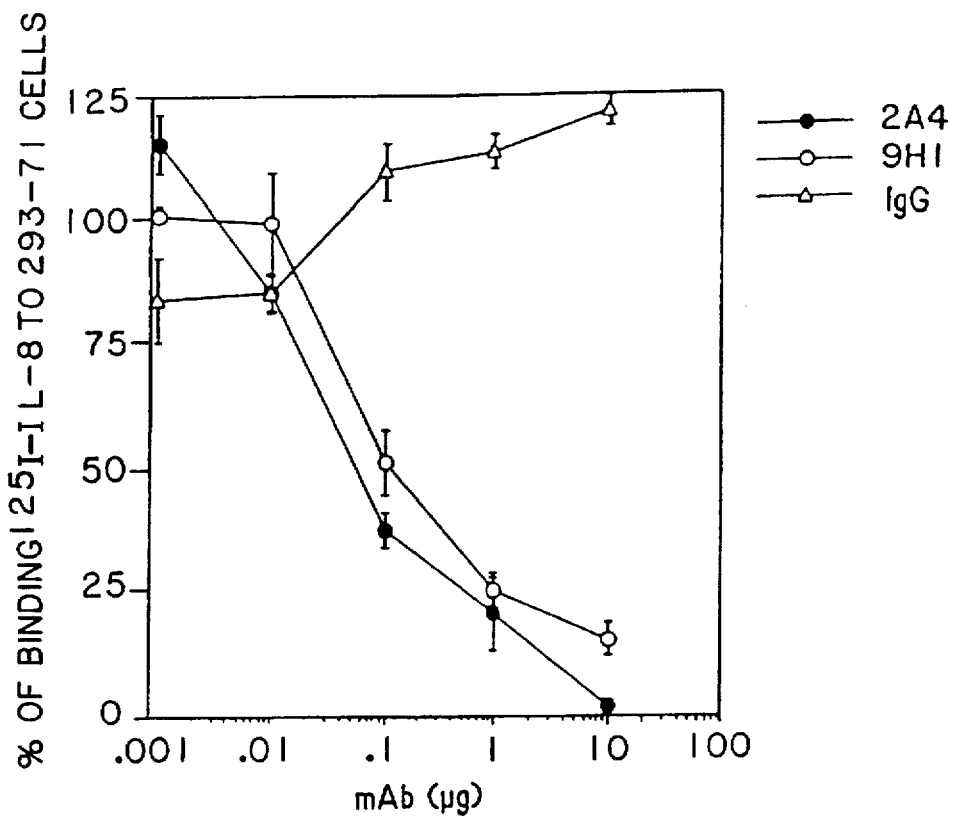
FIGS. 8A and 8B show the inhibition of $^{125}$I-labeled IL-8 binding to human neutrophils (FIG. 8B) and to 293 transfected cells expressing IL8R-A (293-71) (FIG. 8A) by various concentrations of 2A4 (filled circles), 9H1 (open circles), IgG (open triangles), and, for FIG. 8B, no antibody (filled squares). The experiment using human neutrophils was carried out in the presence of various concentrations of MGSA.
Figure 8B:
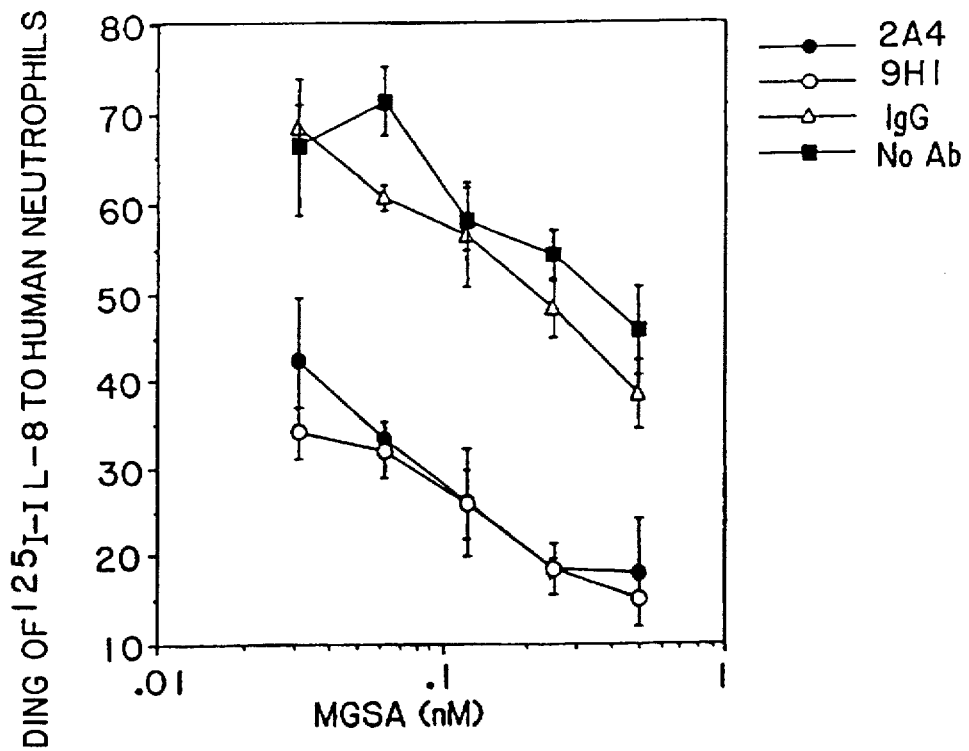

It was further investigated whether monoclonal antibodies 2A4 and 9H1 could block IL-8 binding onto human neutrophils in the presence of various concentrations of MGSA, known to bind to IL8R-B. The addition of 475 pM of MGSA inhibited approximately 50% of IL-8 binding to human neutrophils (FIG. 8). In the presence of 475 pM of MGSA, monoclonal antibodies 2A4 and 9H1 could block up to 80% of the IL-8 binding to human neutrophils, while the control monoclonal antibody showed no further inhibition beyond that observed with MGSA alone. Thus, it was concluded that monoclonal antibodies 2A4 and 9H1 could block the binding of IL-8 to IL8R-A on human neutrophils.

Epitope mapping of the IL8R-A specific monoclonal antibodies

Figure 9A:
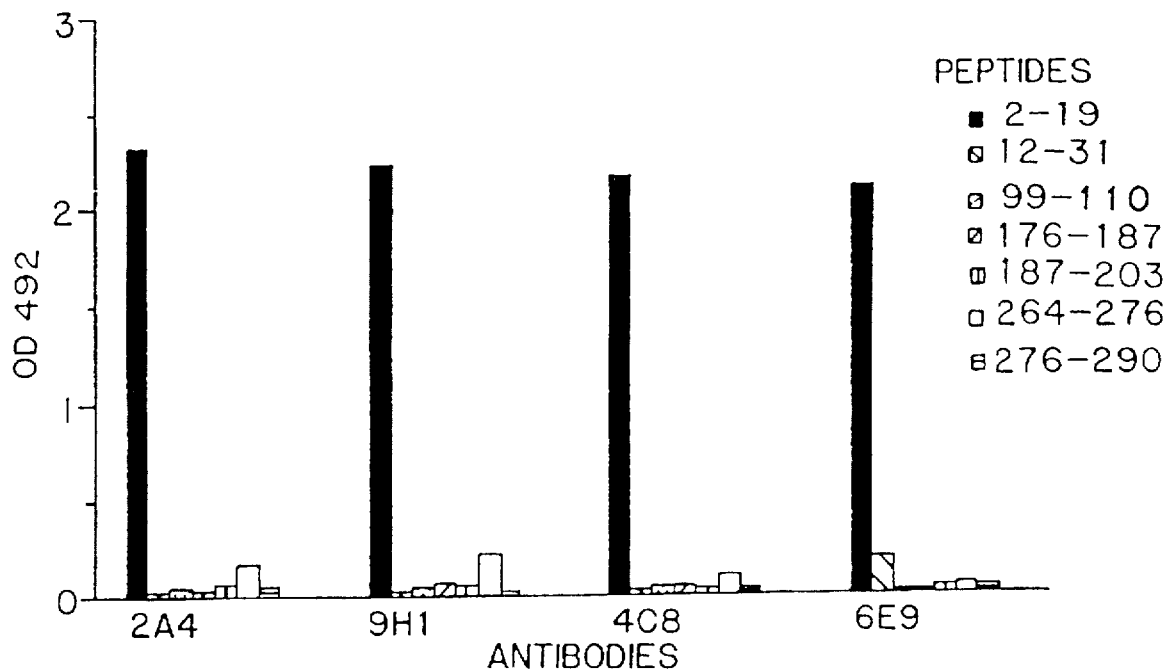
FIGS. 9A and 9B show the binding of monoclonal antibodies 2A4, 9H1, 4C8, 6E9, and an IgG1 control to various synthetic peptides as determined by ELISA. ELISA plates were coated with 2 µg/ml of peptides. Experiments were done in triplicates.

The epitopes recognized by these monoclonal antibodies were mapped by investigating the binding of these antibodies to synthetic peptides by ELISA (FIGS. 9A and 9B) and alanine mutants of IL8R-A by FACS (Table 3). Surprisingly, both blocking and non-blocking monoclonal antibodies bound to the N-terminal peptide consisting of amino acids 2-19, but did not bind to other peptides covering different portions of extracellular loops of the receptor (FIG. 9A).

Figure 9B:
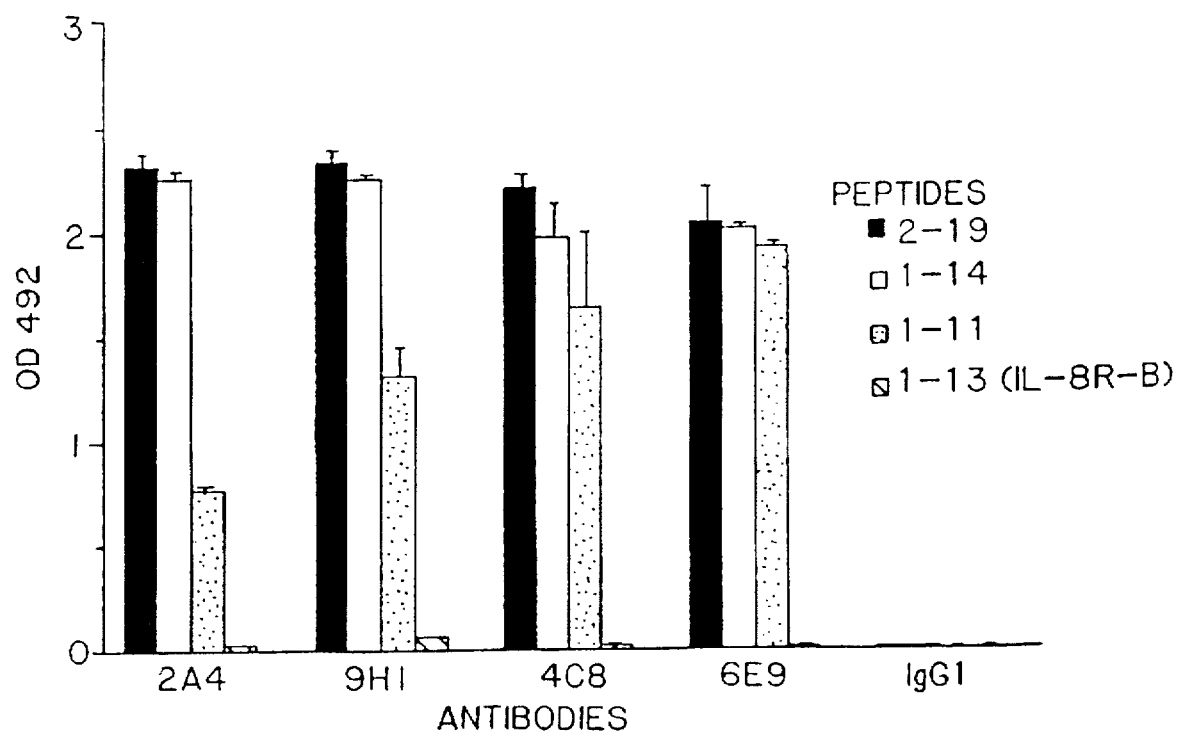

The binding of monoclonal antibodies to shorter peptides consisting of residues 1–11 and 1–14 in ELISA is shown in FIG. 9B. All four monoclonal antibodies bound well to peptide 1-14. However, the binding of the blocking monoclonal antibodies, 2A4 and 9H1, to peptide 1-11 was only 22% and 60% of the binding to peptide 2-19, respectively. In contrast, the binding of the non-blocking monoclonal antibodies 4C8 and 6E9 to peptide 1-11 was approximately 80% and 95% of the binding to peptide 2-19, respectively. From these results, it was concluded that epitopes of monoclonal antibodies 4C8 and 6E9 are localized within amino acids 2-11, while those of monoclonal antibodies 2A4 and 9H1 are localized within amino acids 2-14.

TABLE 3

Flow Cytometry Analysis of Antibodies with Cells Expressing Mutant IL-8 Type A Receptor

| Amino Acid Position | Change | | FACS Analysis | | | |
|---|---|---|---|---|---|---|
| | From | To | 2A4 | 9H1 | 4C8 | 6E9 |
| 6 | D | A | − | − | + | + |
| 11 | D | A | ++ | ++ | + | + |
| 13–14 | DD | A | ++ | ++ | + | ++ |
| 24–26 | DED | AAA | ++ | ++ | ++ | + |

FACS Result: - (mean FL channel 0–10), + (Mean FL channel 10–100, ++ (Mean FL channel 100–1000)
A (Alanine), D (Aspartic acid), K (Lysine), E (Glutamic Acid)

The binding epitopes of these monoclonal antibodies were further investigated by analyzing their binding to IL8R-A mutants by FACS (Table 3). Neither monoclonal antibody 2A4 nor 9H1 could bind to the IL8R-A mutant when the aspartic acid at position 6 was substituted with alanine, suggesting Asp6 plays an important role in the binding of these blocking antibodies. This result further suggests that the conformation of the N-terminal end of the IL8R-A may play a role in the binding of these blocking monoclonal antibodies.

Conclusion

IL-8 is a potent neutrophil chemotactic factor and has been implicated as a key mediator of neutrophil influx in many inflammatory diseases. IL-8 has been detected in many biological fluids from patients with a variety of acute and chronic inflammatory diseases such as arthritis, emphysema, cystic fibrosis, ulcerative colitis, chronic bronchitis, and bronchiectasis. Koch et al., *J. Immunol.*, 147: 2187-2195 (1991); Koch et al., *Science*, 258: 1798-1801 (1992); Terkeltaub et al., *Arthr. and Rheum.*, 34: 894 (1991); Mahida et al., *Clin. Science*, 82: 273-275 (1992); Broaddus et al., *Am. Rev. Resp.*, 146: 825 (1992). In vitro neutralization of the IL-8 in these biological fluids significantly reduces the overall chemotactic activity in the fluid. Further, the role of IL-8 is implicated in inflammatory conditions where the cellular infiltrate is predominantly neutrophil-rich, including gout, rheumatoid arthritis, adult respiratory distress syndrome, emphysema, glomerular nephritis, myocardial infarction, inflammatory bowel disease, and asthma. Lindley et al., *Adv. Exp. Med.*, 305: 147-156 (1991). However, to what extent IL-8 contributes to inflammation in vivo has yet to be determined.

Various monoclonal antibodies directed against IL-8 have been defined, including those reported by Sticherling et al., *J. Immunol.*, 143: 1628-1634 (1989).

It is anticipated that an antagonist to IL8R-A will be more effective in blocking the effect of IL-8 function in vivo than an antagonist to IL-8 for the following reasons: IL-8 is relatively long-lasting and resistant to proteases, possibly making it difficult to block IL-8 completely in vivo, the IL8R-A expression is dynamically regulated by the ligand itself, and the rapid recycling of IL-8 receptors may be essential for the chemotactic response of neutrophils and tissue damage during inflammation, caused by activated neutrophils. Thus, monoclonal antibodies to IL8R-A expressed on human neutrophils were generated with the ultimate goal of identifying neutralizing monoclonal antibodies that could be tested as receptor antagonists of various inflammation in in vivo models.

The antibody responses to different extracellular portions of IL8R-A were induced using several synthetic peptides covering the extracellular domains of IL8R-A or IL8R-A-transfected cells as immunogens. Both methods of immunization allowed generation of monoclonal antibodies recognizing IL8R-A on human neutrophils (FIG. 6). It was much harder to generate monoclonal antibodies specific for IL8R-A by using transfected cells as an immunogen; however, monoclonal antibodies generated using transfected cells tended to have higher affinities to IL8R-A and showed blocking activities.

Polyclonal antibody responses were able to be induced to all seven peptides covering the extracellular domains of IL8R-A, residues 2-19, 12-31, 99-110, 176-186, 187-203, 265-277, and 277-291. However, only the polyclonal antibodies to peptide 2-19 recognize IL8R-A on cells. This suggests that the N-terminal amino acids may be the most immunogenic or that the most likely immunogenic sites have conformational epitopes.

A 77% sequence identity between IL8R-A and IL8R-B was reported by Holmes et al., supra; however, the antibodies herein were specific for IL8R-A. IL8R-A does not recognize IL-1, TNF-α, MCAF, fMLP, C5α, PAF, and LTB4, but does recognize two other members of the C-X-C family, namely, MGSA and NAP-2. Holmes et al., supra. A recent study shows that both receptors bind IL-8 equally well with a high affinity but differ in their affinity to MGSA. Murphy and Tiffany, supra. Monoclonal antibodies 2A4 and 9H1 block 100% of the IL-8 binding to transfected 293 cells, 35-40% of the IL-8 binding to human neutrophils, and approximately 80% of IL-8 binding to human neutrophils in the presence of MGSA, which presumably blocked IL-8 binding to IL8R-B. Thus, the blocking monoclonal antibodies herein interfere with the interaction between IL-8 and IL8R-A, but not with the interaction between IL-8 and IL8R-B. Both monoclonal antibodies 4C8 and 6E9 showed no blocking activities in IL-8 binding to both transfected cells and human neutrophils.

The finding that both blocking and non-blocking monoclonal antibodies bind to the N-terminal amino acid residues 1-14 (FIG. 9A) is consistent with the report that the N-terminal amino acid sequence of IL8R-A plays an important role in interacting with IL-8. Gayle et al., *J. Biol. Chem.*, 268: 7283-7289 (1993). Further epitope mapping analysis showed some differences in the binding characteristics between blocking and non-blocking monoclonal antibodies. The epitopes of blocking monoclonal antibodies 2A4 and 9H1 were mapped within residues 2-14 of the receptor, while those of non-blocking monoclonal antibodies 4C8 and 6E9 were within 2-11 amino acid residues. The binding study using various alanine mutants shows that the aspartic acid at position 6 plays an important role in the binding of the blocking monoclonal antibodies, but not of the non-blocking monoclonal antibodies. This suggests that this negatively charged aspartic acid may be located at (or near to) the binding site of IL-8. It has been shown that positively charged IL-8 residues $E_4$, $L_5$, $R_6$ are essential for IL-8 binding to its receptors on human neutrophils by alanine-scanning mutagenesis (Hébert et al., *J. Biol. Chem.*, 266: 18989-18994 [1991]) and synthesis of N-terminal truncated variants (Clark-Lewis et al., *J. Biol. Chem.*, 266: 23128-23134 [1991]; Moser et al., *J. Biol. Chem.*, 268: 7125-7128 [1993]). Without being limited to any one theory, it is believed that the negatively charged amino acid at position 6 in IL8R-A is in a direct or close interaction with the positively charged amino acids, $E_4$, $L_5$, $R_6$ in IL-8, so that the binding of blocking monoclonal antibodies is influenced by the tertiary structure of the receptor.

The N-terminal portion and the second extracellular portion of the IL8R-A appears to be highly glycosylated, especially within amino acids 2-19 of the receptor, where there are six potential glycosylation sites (FIG. 6). However, all of the monoclonal antibodies herein, whether generated by immunization of synthetic peptides or of transfected cells, bound to the synthetic peptide covering amino acids 1-14. This suggests that carbohydrates may not play an important role in the binding of these monoclonal antibodies.

EXAMPLE 4

Figure 10:
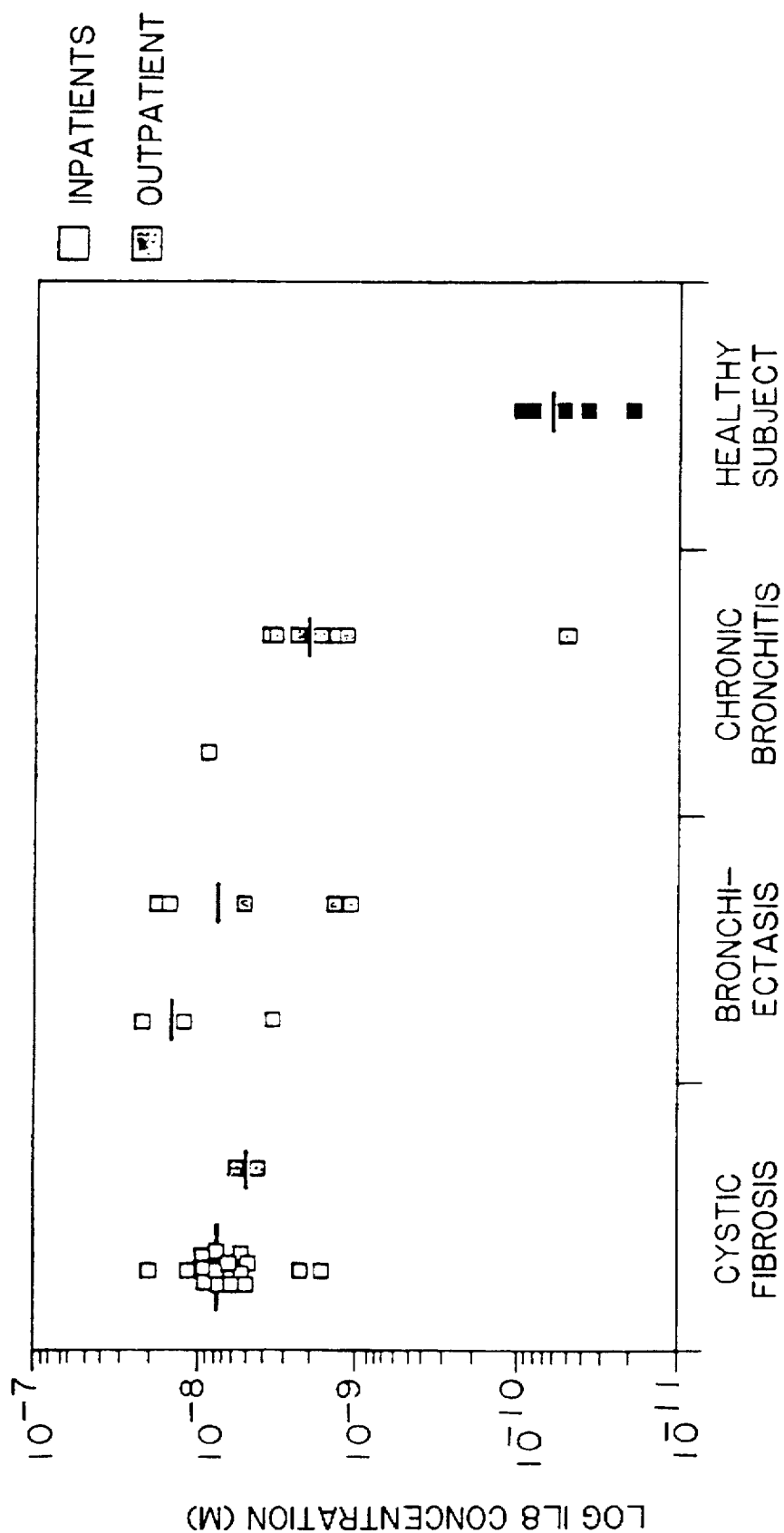
FIG. 10 shows the concentrations of IL-8 in sputum from various patients with chronic airway inflammation (cystic fibrosis, bronchiectasis, and chronic bronchitis) and induced sputum for healthy subjects, where the open squares are in-patients and the shaded squares are out-patients.

IL-8 was found to be present at high concentration and is the major neutrophil chemotactic factor in sputum from patients with chronic bronchitis, bronchiectasis, and cystic fibrosis. FIG. 10 shows the concentration of IL-8 in sputum from patients with chronic airway diseases and in sputum induced from healthy patients.

An ELISA is developed to measure rabbit IL-8 concentration using a double monoclonal antibody technique where one antibody is used as the coat and the other is the biotinylated detection antibody. In the assay buffer the sensitivity is <12 pg/ml (linear range 12-1000 pg/ml). In 10% rabbit serum the sensitivity is 14 pg/ml (linear range 14-1000 pg/ml).

One of the two antibodies 2A4 and 9H1 described above is injected intravenously every two weeks in a dose of 1–15 mg/kg in patients having either asthma, chronic bronchitis, bronchiectesis, rheumatoid arthritis, or ulcerative colitis. For treating an acute indication, adult respiratory distress syndrome, a dose of 10–100 mg/kg of either one of the antibodies is injected a single time intravenously. It would be expected that the anti-IL8R-A antibodies that block IL8R-A activity (MAbs 2A4 and 9H1) would be effective in reducing the inflammation associated with each of the disorders described above. The antibodies are also expected to be efficacious in treating human pleurisy, vasculitis, alveolitis, and pneumonia.

Deposit of Materials

The following hybridomas have been deposited with the American Type Culture Collection, 12301 Parklawn Drive, Rockville, Md., USA (ATCC):

| Cell Lines | ATCC Accession No. | Deposit Date |
|---|---|---|
| 2A4 | HB 11377 | June 8, 1993 |
| 9H1 | HB 11376 | June 8, 1993 |

These deposits were made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. These cell lines will be made available by ATCC under the terms of the Budapest Treaty, and subject to an agreement between Genentech, Inc. and ATCC, which assures permanent and unrestricted availability of the cell lines to the public upon issuance of the pertinent U.S. patent or upon laying open to the public of any U.S. or foreign patent application, whichever comes first, and assures availability of the cell lines to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the deposited cell lines should be lost or destroyed when cultivated under suitable conditions, they will be promptly replaced on notification with a specimen of the same cell line. Availability of the deposited cell lines is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines deposited, since the deposited embodiments are intended as illustrations of one aspect of the invention and any cell lines that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An antibody that is capable of binding to an extracellular region of a platelet factor 4 superfamily receptor (PF4AR) polypeptide having the amino acid sequence of FIG. 4 (SEQ ID NO.4).

2. The antibody of claim 1 that is a monoclonal antibody.

3. A composition comprising the antibody of claim 1 and a carrier.

4. The composition of claim 3 that is sterile, for in vitro use.

5. The antibody of claim 1 that is capable of binding to the N-terminal extracellular region of a platelet factor 4 superfamily receptor (PF4AR) polypeptide having the amino acid sequence of FIG. 4 (SEQ ID NO.4).

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1933 nucleotides
        ( B ) TYPE: Nucleic Acid
        ( C ) STRANDEDNESS: Single
        ( D ) TOPOLOGY: Linear ( x i ) SEQUENCE DESCRIPTION: SEQ ID NO:1:

```
CCTGGCCGGT  GCTTCAGTTA  GATCAAACCA  TTGCTGAAAC  TGAAGAGGAC          50

ATGTCAAATA  TTACAGATCC  ACAGATGTGG  GATTTTGATG  ATCTAAATTT         100

CACTGGCATG  CCACCTGCAG  ATGAAGATTA  CAGCCCCTGT  ATGCTAGAAA         150

CTGAGACACT  CAACAAGTAT  GTTGTGATCA  TCGCCTATGC  CCTAGTGTTC         200

CTGCTGAGCC  TGCTGGGAAA  CTCCCTGGTG  ATGCTGGTCA  TCTTATACAG         250

CAGGGTCGGC  CGCTCCGTCA  CTGATGTCTA  CCTGCTGAAC  CTGGCCTTGG         300

CCGACCTACT  CTTTGCCCTG  ACCTTGCCCA  TCTGGGCCGC  CTCCAAGGTG         350

AATGGCTGGA  TTTTTGGCAC  ATTCCTGTGC  AAGGTGGTCT  CACTCCTGAA         400

GGAAGTCAAC  TTCTACAGTG  GCATCCTGCT  GTTGGCCTGC  ATCAGTGTGG         450

ACCGTTACCT  GGCCATTGTC  CATGCCACAC  GCACACTGAC  CCAGAAGCGT         500
```

-continued

| | | | | |
|---|---|---|---|---|
| CACTTGGTCA | AGTTTGTTTG | TCTTGGCTGC | TGGGGACTGT | CTATGAATCT | 550 |
| GTCCCTGCCC | TTCTTCCTTT | TCCGCCAGGC | TTACCATCCA | AACAATTCCA | 600 |
| GTCCAGTTTG | CTATGAGGTC | CTGGGAAATG | ACACAGCAAA | ATGGCGGATG | 650 |
| GTGTTGCGGA | TCCTGCCTCA | CACCTTTGGC | TTCATCGTGC | CGCTGTTTGT | 700 |
| CATGCTGTTC | TGCTATGGAT | TCACCCTGCG | TACACTGTTT | AAGGCCCACA | 750 |
| TGGGGCAGAA | GCACCGAGCC | ATGAGGGTCA | TCTTTGCTGT | CGTCCTCATC | 800 |
| TTCCTGCTTT | GCTGGCTGCC | CTACAACCTG | GTCCTGCTGG | CAGACACCCT | 850 |
| CATGAGGACC | CAGGTGATCC | AGGAGACCTG | TGAGCGCCGC | AACAACATCG | 900 |
| GCCGGGCCCT | GGATGCCACT | GAGATTCTGG | GATTCTCCA | TAGCTGCCTC | 950 |
| AACCCCATCA | TCTACGCCTT | CATCGGCCAA | AATTTTCGCC | ATGGATTCCT | 1000 |
| CAAGATCCTG | GCTATGCATG | GCCTGGTCAG | CAAGGAGTTC | TTGGCACGTC | 1050 |
| ATCGTGTTAC | CTCCTACACT | TCTTCGTCTG | TCAATGTCTC | TTCCAACCTC | 1100 |
| TGAAAACCAT | CGATGAAGGA | ATATCTCTTC | TCAGAAGGAA | AGAATAACCA | 1150 |
| ACACCCTGAG | GTTGTGTGTG | GAAGGTGATC | TGGCTCTGGA | CAGGCACTAT | 1200 |
| CTGGGTTTTG | GGGGACGCT | ATAGGATGTG | GGGAAGTTAG | GAACTGGTGT | 1250 |
| CTTCAGGGGC | CACACCAACC | TTCTGAGGAG | CTGTTGAGGT | ACCTCCAAGG | 1300 |
| ACCGGCCTTT | GCACCTCCAT | GGAAACGAAG | CACCATCATT | CCCGTTGAAC | 1350 |
| GTCACATCTT | TAACCCACTA | ACTGGCTAAT | TAGCATGGCC | ACATCTGAGC | 1400 |
| CCCGAATCTG | ACATTAGATG | AGAGAACAGG | GCTGAAGCTG | TGTCCTCATG | 1450 |
| AGGGCTGGAT | GCTCTCGTTG | ACCCTCACAG | GAGCATCTCC | TCAACTCTGA | 1500 |
| GTGTTAAGCG | TTGAGCCACC | AAGCTGGTGG | CTCTGTGTGC | TCTGATCCGA | 1550 |
| GCTCAGGGGG | GTGGTTTTCC | CATCTCAGGT | GTGTTGCAGT | GTCTGCTGGA | 1600 |
| GACATTGAGG | CAGGCACTGC | CAAAACATCA | ACCTGCCAGC | TGGCCTTGTG | 1650 |
| AGGAGCTGGA | AACACATGTT | CCCCTTGGGG | GTGGTGGATG | AACAAAGAGA | 1700 |
| AAGAGGGTTT | GGAAGCCAGA | TCTATGCCAC | AAGAACCCCC | TTTACCCCCA | 1750 |
| TGACCAACAT | CGCAGACACA | TGTGCTGGCC | ACCTGCTGAG | CCCCAAGTGG | 1800 |
| AACGAGACAA | GCAGCCCTTA | GCCCTTCCCC | TCTGCAGCTT | CCAGGCTGGC | 1850 |
| GTGCAGCATC | AGCATCCCTA | GAAAGCCATG | TGCAGCCACC | AGTCCATTGG | 1900 |
| GCAGGCAGAT | GTTCCTAATA | AAGCTTCTGT | TCC | | 1933 |

( 2 ) INFORMATION FOR SEQ ID NO:2:

( i ) SEQUENCE CHARACTERISTICS:
        ( A ) LENGTH: 350 amino acids
        ( B ) TYPE: Amino Acid
        ( D ) TOPOLOGY: Linear ( x i ) SEQUENCE DESCRIPTION: SEQ ID NO:2:

```
Met  Ser  Asn  Ile  Thr  Asp  Pro  Gln  Met  Trp  Asp  Phe  Asp  Asp  Leu
 1              5                        10                        15

Asn  Phe  Thr  Gly  Met  Pro  Pro  Ala  Asp  Glu  Asp  Tyr  Ser  Pro  Cys
               20                        25                        30

Met  Leu  Glu  Thr  Glu  Thr  Leu  Asn  Lys  Tyr  Val  Val  Ile  Ile  Ala
               35                        40                        45

Tyr  Ala  Leu  Val  Phe  Leu  Leu  Ser  Leu  Leu  Gly  Asn  Ser  Leu  Val
               50                        55                        60
```

| | | | | | | | | | | | | | | |
|---|---|---|---|---|---|---|---|---|---|---|---|---|---|---|
|Met|Leu|Val|Ile|Leu<br>65|Tyr|Ser|Arg|Val|Gly<br>70|Arg|Ser|Val|Thr|Asp<br>75|
|Val|Tyr|Leu|Leu|Asn<br>80|Leu|Ala|Leu|Ala|Asp<br>85|Leu|Leu|Phe|Ala|Leu<br>90|
|Thr|Leu|Pro|Ile|Trp<br>95|Ala|Ala|Ser|Lys|Val<br>100|Asn|Gly|Trp|Ile|Phe<br>105|
|Gly|Thr|Phe|Leu|Cys<br>110|Lys|Val|Val|Ser|Leu<br>115|Leu|Lys|Glu|Val|Asn<br>120|
|Phe|Tyr|Ser|Gly|Ile<br>125|Leu|Leu|Leu|Ala|Cys<br>130|Ile|Ser|Val|Asp|Arg<br>135|
|Tyr|Leu|Ala|Ile|Val<br>140|His|Ala|Thr|Arg|Thr<br>145|Leu|Thr|Gln|Lys|Arg<br>150|
|His|Leu|Val|Lys|Phe<br>155|Val|Cys|Leu|Gly|Cys<br>160|Trp|Gly|Leu|Ser|Met<br>165|
|Asn|Leu|Ser|Leu|Pro<br>170|Phe|Phe|Leu|Phe|Arg<br>175|Gln|Ala|Tyr|His|Pro<br>180|
|Asn|Asn|Ser|Ser|Pro<br>185|Val|Cys|Tyr|Glu|Val<br>190|Leu|Gly|Asn|Asp|Thr<br>195|
|Ala|Lys|Trp|Arg|Met<br>200|Val|Leu|Arg|Ile|Leu<br>205|Pro|His|Thr|Phe|Gly<br>210|
|Phe|Ile|Val|Pro|Leu<br>215|Phe|Val|Met|Leu|Phe<br>220|Cys|Tyr|Gly|Phe|Thr<br>225|
|Leu|Arg|Thr|Leu|Phe<br>230|Lys|Ala|His|Met|Gly<br>235|Gln|Lys|His|Arg|Ala<br>240|
|Met|Arg|Val|Ile|Phe<br>245|Ala|Val|Val|Leu|Ile<br>250|Phe|Leu|Leu|Cys|Trp<br>255|
|Leu|Pro|Tyr|Asn|Leu<br>260|Val|Leu|Leu|Ala|Asp<br>265|Thr|Leu|Met|Arg|Thr<br>270|
|Gln|Val|Ile|Gln|Glu<br>275|Thr|Cys|Glu|Arg|Arg<br>280|Asn|Asn|Ile|Gly|Arg<br>285|
|Ala|Leu|Asp|Ala|Thr<br>290|Glu|Ile|Leu|Gly|Phe<br>295|Leu|His|Ser|Cys|Leu<br>300|
|Asn|Pro|Ile|Ile|Tyr<br>305|Ala|Phe|Ile|Gly|Gln<br>310|Asn|Phe|Arg|His|Gly<br>315|
|Phe|Leu|Lys|Ile|Leu<br>320|Ala|Met|His|Gly|Leu<br>325|Val|Ser|Lys|Glu|Phe<br>330|
|Leu|Ala|Arg|His|Arg<br>335|Val|Thr|Ser|Tyr|Thr<br>340|Ser|Ser|Ser|Val|Asn<br>345|
|Val|Ser|Ser|Asn|Leu<br>350| | | | | | | | | | |

( 2 ) INFORMATION FOR SEQ ID NO:3:

( i ) SEQUENCE CHARACTERISTICS:
        ( A ) LENGTH: 1737 nucleotides
        ( B ) TYPE: Nucleic Acid
        ( C ) STRANDEDNESS: Single
        ( D ) TOPOLOGY: Linear ( x i ) SEQUENCE DESCRIPTION: SEQ ID NO:3:

```
GAATTCCAGT GTGCTGGCGG CGCGGCGCAA AGTGACGCCG AGGGCCTGAG           50

TGCTCCAGTA GCCACCGCAT CTGGAGAACC AGCGGTTACC ATGGAGGGGA          100

TCAGTATATA CACTTCAGAT AACTACACCG AGGAAATGGG CTCAGGGGAC          150

TATGACTCCA TGAAGGAACC CTGTTTCCGT GAAGAAAATG CTAATTTCAA          200

TAAAATCTTC CTGCCCACCA TCTACTCCAT CATCTTCTTA ACTGGCATTG          250
```

```
TGGGCAATGG  ATTGGTCATC  CTGGTCATGG  GTTACCAGAA  GAAACTGAGA        300

AGCATGACGG  ACAAGTACAG  GCTGCACCTG  TCAGTGGCCG  ACCTCCTCTT        350

TGTCATCACG  CTTCCCTTCT  GGGCAGTTGA  TGCCGTGGCA  AACTGGTACT        400

TTGGGAACTT  CCTATGCAAG  GCAGTCCATG  TCATCTACAC  AGTCAACCTC        450

TACAGCAGTG  TCCTCATCCT  GGCCTTCATC  AGTCTGGACC  GCTACCTGGC        500

CATCGTCCAC  GCCACCAACA  GTCAGAGGCC  AAGGAAGCTG  TTGGCTGAAA        550

AGGTGGTCTA  TGTTGGCGTC  TGGATCCCTG  CCCTCCTGCT  GACTATTCCC        600

GACTTCATCT  TTGCCAACGT  CAGTGAGGCA  GATGACAGAT  ATATCTGTGA        650

CCGCTTCTAC  CCCAATGACT  GTGGGTGGT   TGTGTTCCAG  TTTCAGCACA        700

TCATGGTTGG  CCTTATCCTG  CCTGGTATTG  TCATCCTGTC  CTGCTATTGC        750

ATTATCATCT  CCAAGCTGTC  ACACTCCAAG  GGCCACCAGA  AGCGCAAGGC        800

CCTCAAGACC  ACAGTCATCC  TCATCCTGGC  TTTCTTCGCC  TGTTGGCTGC        850

CTTACTACAT  TGGGATCAGC  ATCGACTCCT  TCATCCTCCT  GGAAATCATC        900

AAGCAAGGGT  GTGAGTTTGA  GAACACTGTG  CACAAGTGGA  TTTCCATCAC        950

CGAGGCCCTA  GCTTCTTCC   ACTGTTGTCT  GAACCCCATC  CTCTATGCTT       1000

TCCTTGGAGC  CAAATTTAAA  ACCTCTGCCC  AGCACGCACT  CACCTCTGTG       1050

AGCAGAGGGT  CCAGCCTCAA  GATCCTCTCC  AAAGGAAAGC  GAGGTGGACA       1100

TTCATCTGTT  TCCACTGAGT  CTGAGTCTTC  AAGTTTTCAC  TCCAGCTAAC       1150

ACAGATGTAA  AAGACTTTTT  TTTATACGAT  AAATAACTTT  TTTTTAAGTT       1200

ACACATTTTT  CAGATATAAA  AGACTGACCA  ATATTGTACA  GTTTTTATTG       1250

CTTGTTGGAT  TTTTGTCTTG  TGTTTCTTTA  GTTTTGTGA   AGTTTAATTG       1300

ACTTATTTAT  ATAAATTTTT  TTGTTTCAT   ATTGATGTGT  GTCTAGGCAG       1350

GACCTGTGGC  CAAGTTCTTA  GTTGCTGTAT  GTCTCGTGGT  AGGACTGTAG       1400

AAAAGGGAAC  TGAACATTCC  AGAGCGTGTA  GTGAATCACG  TAAAGCTAGA       1450

AATGATCCCC  AGCTGTTTAT  GCATAGATAA  TCTCTCCATT  CCCGTGGAAC       1500

GTTTTTCCTG  TTCTTAAGAC  GTGATTTTGC  TGTAGAAGAT  GGCACTTATA       1550

ACCAAAGCCC  AAAGTGGTAT  AGAAATGCTG  GTTTTCAGT   TTTCAGGAGT       1600

GGGTTGATTT  CAGCACCTAC  AGTGTACAGT  CTTGTATTAA  GTTGTTAATA       1650

AAAGTACATG  TTAAACTTAA  AAAAAAAAA   AAAAAAAAA   AAAAAAAAA        1700

AAAAAAAAA   AAAGCGGCCG  CCAGCACACT  GGAATTC                      1737
```

( 2 ) INFORMATION FOR SEQ ID NO:4:

( i ) SEQUENCE CHARACTERISTICS:
        ( A ) LENGTH: 352 amino acids
        ( B ) TYPE: Amino Acid
        ( D ) TOPOLOGY: Linear ( x i ) SEQUENCE DESCRIPTION: SEQ ID NO:4:

```
Met  Glu  Gly  Ile  Ser  Ile  Tyr  Thr  Ser  Asp  Asn  Tyr  Thr  Glu  Glu
 1             5                      10                       15

Met  Gly  Ser  Gly  Asp  Tyr  Asp  Ser  Met  Lys  Glu  Pro  Cys  Phe  Arg
               20                      25                       30

Glu  Glu  Asn  Ala  Asn  Phe  Asn  Lys  Ile  Phe  Leu  Pro  Thr  Ile  Tyr
               35                      40                       45
```

| | | | | | | | | | | | | |
|---|---|---|---|---|---|---|---|---|---|---|---|---|
| Ser | Ile | Ile | Phe | Leu<br>50 | Thr | Gly | Ile | Val<br>55 | Gly | Asn | Gly | Leu | Val | Ile<br>60 |
| Leu | Val | Met | Gly | Tyr<br>65 | Gln | Lys | Lys | Leu<br>70 | Arg | Ser | Met | Thr | Asp | Lys<br>75 |
| Tyr | Arg | Leu | His | Leu<br>80 | Ser | Val | Ala | Asp<br>85 | Leu | Leu | Phe | Val | Ile | Thr<br>90 |
| Leu | Pro | Phe | Trp | Ala<br>95 | Val | Asp | Ala | Val<br>100 | Ala | Asn | Trp | Tyr | Phe | Gly<br>105 |
| Asn | Phe | Leu | Cys | Lys<br>110 | Ala | Val | His | Val<br>115 | Ile | Tyr | Thr | Val | Asn | Leu<br>120 |
| Tyr | Ser | Ser | Val | Leu<br>125 | Ile | Leu | Ala | Phe<br>130 | Ile | Ser | Leu | Asp | Arg | Tyr<br>135 |
| Leu | Ala | Ile | Val | His<br>140 | Ala | Thr | Asn | Ser<br>145 | Gln | Arg | Pro | Arg | Lys | Leu<br>150 |
| Leu | Ala | Glu | Lys | Val<br>155 | Val | Tyr | Val | Gly<br>160 | Val | Trp | Ile | Pro | Ala | Leu<br>165 |
| Leu | Leu | Thr | Ile | Pro<br>170 | Asp | Phe | Ile | Phe<br>175 | Ala | Asn | Val | Ser | Glu | Ala<br>180 |
| Asp | Asp | Arg | Tyr | Ile<br>185 | Cys | Asp | Arg | Phe<br>190 | Tyr | Pro | Asn | Asp | Leu | Trp<br>195 |
| Val | Val | Val | Phe | Gln<br>200 | Phe | Gln | His | Ile<br>205 | Met | Val | Gly | Leu | Ile | Leu<br>210 |
| Pro | Gly | Ile | Val | Ile<br>215 | Leu | Ser | Cys | Tyr<br>220 | Cys | Ile | Ile | Ile | Ser | Lys<br>225 |
| Leu | Ser | His | Ser | Lys<br>230 | Gly | His | Gln | Arg<br>235 | Lys | Ala | Leu | Lys | Thr<br>240 |
| Thr | Val | Ile | Leu | Ile<br>245 | Leu | Ala | Phe | Phe<br>250 | Ala | Cys | Trp | Leu | Pro | Tyr<br>255 |
| Tyr | Ile | Gly | Ile | Ser<br>260 | Ile | Asp | Ser | Phe<br>265 | Ile | Leu | Leu | Glu | Ile | Ile<br>270 |
| Lys | Gln | Gly | Cys | Glu<br>275 | Phe | Glu | Asn | Thr<br>280 | Val | His | Lys | Trp | Ile | Ser<br>285 |
| Ile | Thr | Glu | Ala | Leu<br>290 | Ala | Phe | Phe | His<br>295 | Cys | Cys | Leu | Asn | Pro | Ile<br>300 |
| Leu | Tyr | Ala | Phe | Leu<br>305 | Gly | Ala | Lys | Phe<br>310 | Lys | Thr | Ser | Ala | Gln | His<br>315 |
| Ala | Leu | Thr | Ser | Val<br>320 | Ser | Arg | Gly | Ser<br>325 | Ser | Leu | Lys | Ile | Leu | Ser<br>330 |
| Lys | Gly | Lys | Arg | Gly<br>335 | Gly | His | Ser | Ser<br>340 | Val | Ser | Thr | Glu | Ser | Glu<br>345 |
| Ser | Ser | Ser | Phe | His<br>350 | Ser | Ser<br>352 | | | | | | | |

( 2 ) INFORMATION FOR SEQ ID NO:5:

( i ) SEQUENCE CHARACTERISTICS:
        ( A ) LENGTH: 1679 nucleotides
        ( B ) TYPE: Nucleic Acid
        ( C ) STRANDEDNESS: Single
        ( D ) TOPOLOGY: Linear ( x i ) SEQUENCE DESCRIPTION: SEQ ID NO:5:

```
GAATTCCAGT GTGCTGGCGG CCGCCCAGTG TGCTGGCGGC GGCAGTTGAG           50

GGAAAGGACA GAGGTTATGA GTGCCTGCAA GAGTGGCAGC CTGGAGTAGA          100

GAAAACACTA AAGGTGGAGT CAAAAGACCT GAGTTCAAGT CCCAGCTCTG          150
```

-continued

| | | | | |
|---|---|---|---|---|
| CCACTGGTTA | GCTGTGGGAT | CTCGGAAAAG | ACCCAGTGAA | AAAAAAAAAA | 200 |
| AAAGTGATGA | GTTGTGAGGC | AGGTCGCGGC | CCTACTGCCT | CAGGAGACGA | 250 |
| TGCGCAGCTC | ATTTGCTTAA | ATTTGCAGCT | GACGGCTGCC | ACCTCTCTAG | 300 |
| AGGCACCTGG | CGGGGAGCCT | CTCAACATAA | GACAGTGACC | AGTCTGGTGA | 350 |
| CTCACAGCCG | GCACAGCCAT | GAACTACCCG | CTAACGCTGG | AAATGGACCT | 400 |
| CGAGAACCTG | GAGGACCTGT | TCTGGGAACT | GGACAGATTG | GACAACTATA | 450 |
| ACGACACCTC | CCTGGTGGAA | AATCATCTCT | GCCCTGCCAC | AGAGGGGCCC | 500 |
| CTCATGGCCT | CCTTCAAGGC | CGTGTTCGTG | CCCGTGGCCT | ACAGCCTCAT | 550 |
| CTTCCTCCTG | GGCGTGATCG | GCAACGTCCT | GGTGCTGGTG | ATCCTGGAGC | 600 |
| GGCACCGGCA | GACACGCAGT | TCCACGGAGA | CCTTCCTGTT | CCACCTGGCC | 650 |
| GTGGCCGACC | TCCTGCTGGT | CTTCATCTTG | CCCTTTGCCG | TGGCCGAGGG | 700 |
| CTCTGTGGGC | TGGGTCCTGG | GGACCTTCCT | CTGCAAAACT | GTGATTGCCC | 750 |
| TGCACAAAGT | CAACTTCTAC | TGCAGCAGCC | TGCTCCTGGC | CTGCATCGCC | 800 |
| GTGGACCGCT | ACCTGGCCAT | TGTCCACGCC | GTCCATGCCT | ACCGCCACCG | 850 |
| CCGCCTCCTC | TCCATCCACA | TCACCTGTGG | GACCATCTGG | CTGGTGGGCT | 900 |
| TCCTCCTTGC | CTTGCCAGAG | ATTCTCTTCG | CCAAAGTCAG | CCAAGGCCAT | 950 |
| CACAACAACT | CCCTGCCACG | TTGCACCTTC | TCCCAAGAGA | ACCAAGCAGA | 1000 |
| AACGCATGCC | TGGTTCACCT | CCCGATTCCT | CTACCATGTG | GCGGGATTCC | 1050 |
| TGCTGCCCAT | GCTGGTGATG | GGCTGGTGCT | ACGTGGGGGT | AGTGCACAGG | 1100 |
| TTGCGCCAGG | CCCAGCGGCG | CCCTCAGCGG | CAGAAGGCAG | TCAGGGTGGC | 1150 |
| CATCCTGGTG | ACAAGCATCT | TCTTCCTCTG | CTGGTCACCC | TACCACATCG | 1200 |
| TCATCTTCCT | GGACACCCTG | GCGAGGCTGA | AGGCCGTGGA | CAATACCTGC | 1250 |
| AAGCTGAATG | GCTCTCTCCC | CGTGGCCATC | ACCATGTGTG | AGTTCCTGGG | 1300 |
| CCTGGCCCAC | TGCTGCCTCA | ACCCCATGCT | CTACACTTTC | GCCGGCGTGA | 1350 |
| AGTTCCGCAG | TGACCTGTCG | CGGCTCCTGA | CGAAGCTGGG | CTGTACCGGC | 1400 |
| CCTGCCTCCC | TGTGCCAGCT | CTTCCCTAGC | TGGCGCAGGA | GCAGTCTCTC | 1450 |
| TGAGTCAGAG | AATGCCACCT | CTCTCACCAC | GTTCTAGGTC | CCAGTGTCCC | 1500 |
| CTTTTATTGC | TGCTTTTCCT | TGGGGCAGGC | AGTGATGCTG | GATGCTCCTT | 1550 |
| CCAACAGGAG | CTGGGATCCT | AAGGGCTCAC | CGTGGCTAAG | AGTGTCCTAG | 1600 |
| GAGTATCCTC | ATTTGGGGTA | GCTAGAGGAA | CCAACCCCCA | TTTCTAGAAC | 1650 |
| ATCCCGCGGC | CGCCAGCACA | CTGGAATTC | | | 1679 |

( 2 ) INFORMATION FOR SEQ ID NO:6:

( i ) SEQUENCE CHARACTERISTICS:
( A ) LENGTH: 372 amino acids
( B ) TYPE: Amino Acid
( D ) TOPOLOGY: Linear ( x i ) SEQUENCE DESCRIPTION: SEQ ID NO:6:

```
Met  Asn  Tyr  Pro  Leu  Thr  Leu  Glu  Met  Asp  Leu  Glu  Asn  Leu  Glu
 1              5                   10                  15

Asp  Leu  Phe  Trp  Glu  Leu  Asp  Arg  Leu  Asp  Asn  Tyr  Asn  Asp  Thr
                20                  25                  30

Ser  Leu  Val  Glu  Asn  His  Leu  Cys  Pro  Ala  Thr  Glu  Gly  Pro  Leu
                35                  40                  45
```

-continued

| | | | | | | | | | | | | |
|---|---|---|---|---|---|---|---|---|---|---|---|---|
| Met | Ala | Ser | Phe | Lys 50 | Ala | Val | Phe | Val | Pro 55 | Val | Ala | Tyr | Ser | Leu 60 |
| Ile | Phe | Leu | Leu | Gly 65 | Val | Ile | Gly | Asn | Val 70 | Leu | Val | Leu | Val | Ile 75 |
| Leu | Glu | Arg | His | Arg 80 | Gln | Thr | Arg | Ser | Ser 85 | Thr | Glu | Thr | Phe | Leu 90 |
| Phe | His | Leu | Ala | Val 95 | Ala | Asp | Leu | Leu | Leu 100 | Val | Phe | Ile | Leu | Pro 105 |
| Phe | Ala | Val | Ala | Glu 110 | Gly | Ser | Val | Gly | Trp 115 | Val | Leu | Gly | Thr | Phe 120 |
| Leu | Cys | Lys | Thr | Val 125 | Ile | Ala | Leu | His | Lys 130 | Val | Asn | Phe | Tyr | Cys 135 |
| Ser | Ser | Leu | Leu | Leu 140 | Ala | Cys | Ile | Ala | Val 145 | Asp | Arg | Tyr | Leu | Ala 150 |
| Ile | Val | His | Ala | Val 155 | His | Ala | Tyr | Arg | His 160 | Arg | Arg | Leu | Leu | Ser 165 |
| Ile | His | Ile | Thr | Cys 170 | Gly | Thr | Ile | Trp | Leu 175 | Val | Gly | Phe | Leu | Leu 180 |
| Ala | Leu | Pro | Glu | Ile 185 | Leu | Phe | Ala | Lys | Val 190 | Ser | Gln | Gly | His | His 195 |
| Asn | Asn | Ser | Leu | Pro 200 | Arg | Cys | Thr | Phe | Ser 205 | Gln | Glu | Asn | Gln | Ala 210 |
| Glu | Thr | His | Ala | Trp 215 | Phe | Thr | Ser | Arg | Phe 220 | Leu | Tyr | His | Val | Ala 225 |
| Gly | Phe | Leu | Leu | Pro 230 | Met | Leu | Val | Met | Gly 235 | Trp | Cys | Tyr | Val | Gly 240 |
| Val | Val | His | Arg | Leu 245 | Arg | Gln | Ala | Gln | Arg 250 | Arg | Pro | Gln | Arg | Gln 255 |
| Lys | Ala | Val | Arg | Val 260 | Ala | Ile | Leu | Val | Thr 265 | Ser | Ile | Phe | Phe | Leu 270 |
| Cys | Trp | Ser | Pro | Tyr 275 | His | Ile | Val | Ile | Phe 280 | Leu | Asp | Thr | Leu | Ala 285 |
| Arg | Leu | Lys | Ala | Val 290 | Asp | Asn | Thr | Cys | Lys 295 | Leu | Asn | Gly | Ser | Leu 300 |
| Pro | Val | Ala | Ile | Thr 305 | Met | Cys | Glu | Phe | Leu 310 | Gly | Leu | Ala | His | Cys 315 |
| Cys | Leu | Asn | Pro | Met 320 | Leu | Tyr | Thr | Phe | Ala 325 | Gly | Val | Lys | Phe | Arg 330 |
| Ser | Asp | Leu | Ser | Arg 335 | Leu | Leu | Thr | Lys | Leu 340 | Gly | Cys | Thr | Gly | Pro 345 |
| Ala | Ser | Leu | Cys | Gln 350 | Leu | Phe | Pro | Ser | Trp 355 | Arg | Arg | Ser | Ser | Leu 360 |
| Ser | Glu | Ser | Glu | Asn 365 | Ala | Thr | Ser | Leu | Thr 370 | Thr | Phe 372 | | | |